(12) United States Patent
Asano et al.

(10) Patent No.: US 12,357,626 B2
(45) Date of Patent: Jul. 15, 2025

(54) ANTHRANILIC ACID-BASED COMPOUND, AND PIN1 INHIBITOR, THERAPEUTIC AGENT FOR INFLAMMATORY DISEASES AND THERAPEUTIC AGENT FOR CANCER THAT USE THE SAME

(71) Applicant: Amenis Bioscience, Inc., Seoul (KR)

(72) Inventors: Tomoichiro Asano, Hiroshima (JP); Yusuke Nakatsu, Hiroshima (JP); Hisanaka Ito, Hachioji (JP); Takayoshi Okabe, Tokyo (JP)

(73) Assignee: Amenis Bioscience, Inc., Seoul (KR)

( * ) Notice: Subject to any disclaimer, the term of this patent is extended or adjusted under 35 U.S.C. 154(b) by 186 days.

(21) Appl. No.: 16/636,758

(22) PCT Filed: Aug. 6, 2018

(86) PCT No.: PCT/JP2018/029497
§ 371 (c)(1),
(2) Date: May 19, 2020

(87) PCT Pub. No.: WO2019/031472
PCT Pub. Date: Feb. 14, 2019

(65) Prior Publication Data
US 2020/0383967 A1    Dec. 10, 2020

(30) Foreign Application Priority Data
Aug. 7, 2017   (JP) .................... 2017-152808

(51) Int. Cl.
| | |
|---|---|
| A61K 31/24 | (2006.01) |
| A61K 31/47 | (2006.01) |
| A61P 1/16 | (2006.01) |
| A61P 35/00 | (2006.01) |
| C07C 233/81 | (2006.01) |
| C07C 311/21 | (2006.01) |
| C07D 215/48 | (2006.01) |

(52) U.S. Cl.
CPC .............. *A61K 31/47* (2013.01); *A61K 31/24* (2013.01); *A61P 1/16* (2018.01); *A61P 35/00* (2018.01); *C07C 233/81* (2013.01); *C07C 311/21* (2013.01); *C07D 215/48* (2013.01)

(58) Field of Classification Search
CPC .................................................. A61K 31/24
See application file for complete search history.

(56) References Cited

U.S. PATENT DOCUMENTS

| | | | |
|---|---|---|---|
| 5,736,487 A | 4/1998 | Sugai et al. | |
| 7,074,831 B2 | 7/2006 | Jönsson et al. | |
| 2002/0165235 A1 | 11/2002 | Lopez-Tapia et al. | |
| 2003/0114499 A1 | 6/2003 | Brendel et al. | |
| 2004/0220235 A1 | 11/2004 | Augelli-Szafran et al. | |
| 2008/0293749 A1 | 11/2008 | Frormann et al. | |

FOREIGN PATENT DOCUMENTS

| | | |
|---|---|---|
| CN | 1176962 | 3/1998 |
| CN | 1378446 | 11/2002 |
| CN | 1527824 | 9/2004 |
| CN | 1529695 | 9/2004 |
| CN | 1914152 | 2/2007 |
| EP | 0795550 | 9/1997 |
| EP | 1225886 | 7/2002 |
| EP | 1379516 | 11/2005 |
| EP | 1399423 | 11/2007 |
| JP | 10-139767 | 5/1998 |
| JP | 2003-504310 | 2/2003 |
| JP | 2004-075614 | 3/2004 |
| JP | 2004-529899 | 9/2004 |
| JP | 2004-533464 | 11/2004 |
| KR | 10-2002-0008224 | 1/2002 |
| KR | 10-0559015 | 3/2006 |
| KR | 10-0863924 | 10/2008 |
| WO | WO 2000/076489 | 12/2000 |

(Continued)

OTHER PUBLICATIONS

American Chemical Society. Chemical Abstract Service. RN 197360-72-8. Entered into STN: Nov. 14, 1997. (Year: 1997).*
American Chemical Society. Chemical Abstract Service. RN 180297-15-8. First entered into STN/date made available to public: Aug. 29, 1996. (Year: 1996).*
Bachman, G.B., et al. (1946) "Synthesis of Substituted Aminobenzacridines," J. Am. Chem. Soc. 68(8):1599-1602.
Baldwin, R.W., et al. (1965) "Further studies on the influence of peripheral ring substitution on the carcino-genicity of tricycloquinazoline," Biochemical Pharmacoloy 14(3):323-331.
Buckman, B.O., et al. (1996) "Solid-phase synthesis of 1,3-dialkyl quinazoline-2,4-diones," Tetrahedron Letters 37(26):4439-4442.
International Search Report PCT/JP2018/029497 (WO 2019/031472) (2018) (5 pages).

(Continued)

*Primary Examiner* — John S Kenyon
(74) *Attorney, Agent, or Firm* — MEDLER FERRO WOODHOUSE & MILLS PLLC

(57) ABSTRACT

The purpose of the invention is to develop, as drug-candidate compounds, a group of novel compounds having the activity of inhibiting functions of Pin1. The invention provides: a compound represented by formula (I) or a salt thereof; and a Pin1 inhibitor, a pharmaceutical composition, a therapeutic or prophylactic agent for inflammatory diseases, a therapeutic or prophylactic agent for cancer, and a therapeutic or prophylactic agent for adiposity that use said compound/salt.

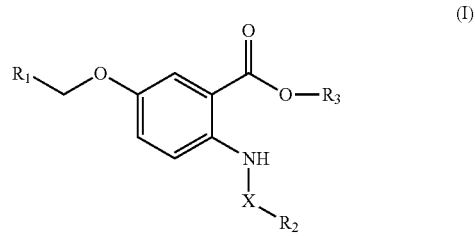

(I)

24 Claims, 4 Drawing Sheets

(56) References Cited

FOREIGN PATENT DOCUMENTS

| WO | WO 2002/070500 | 9/2002 | | |
|---|---|---|---|---|
| WO | WO 2002/100825 | 12/2002 | | |
| WO | WO 2003/004458 | 1/2003 | | |
| WO | WO 2005/075410 | 8/2005 | | |
| WO | WO 2006/040646 | 4/2006 | | |
| WO | WO 2007/028135 | 3/2007 | | |
| WO | WO 2008/097180 | 8/2008 | | |
| WO | WO-2009076747 A1 | * | 6/2009 | ........... A61K 31/444 |
| WO | WO 2016/148145 | 9/2016 | | |
| WO | WO 2017/044551 | 3/2017 | | |

OTHER PUBLICATIONS

Meesala, R., et al. (2010) "*A short route to the synthesis of pyrroloacridines via Ullmann-Goldberg condensation*," Tetrahedron Letters 51(2):422-424.

Proisl, K., et al. (2014) "*Fischer Indolisation of N-(a-ketoacyl)anthranilic acids into 2-(indol-2-carboxamido)benzoic acids and 2-indolyl-3, 1-benzoxazin-4-ones and their NMR study*," Org. Biomol. Chem. 12(47):9650-9664.

Registry (STN) (online), Mar. 5, 2007, CAS: 924823-28-9.

Registry (STN) (online), Jul. 9, 2008, CAS: 1033194-63-6.

Registry (STN) (online), Jun. 9, 2016, CAS: 1928304-05-5.

Registry (STN) (online), Jun. 9, 2016, CAS: 1928308-82-0.

Registry (STN) (online), Aug. 14, 2011, CAS: 1317272-66-4.

Registry (STN) (online), Aug. 17, 2011, CAS: 1318973-99-7.

Spalding, D.P., et al. (1954) "*Heterocyclic Basic Compounds. XV. Benzacridine Derivatives*," J. Org. Chem. 19(3):357-364.

Walse, B., et al. (2008) "*The Structures of Human Dihydroorotate Dehydrogenase with and without Inhibitor Reveal Conformational Flexibility in the Inhibitor and Substrate Binding Sites*," Biochemistry 47(34):8929-8936.

Written Opinion of the International Searching Authority PCT/JP2018/029497 (WO 2019/031472) (2018) (9 pages).

Zidar, N., et al. (2015) "*N-Phenyl-4,5-dibromopyrrolamides and N-Phenylindolamides as ATP Competitive DNA Gyrase B Inhibitors: Design, Synthesis, and Evaluation*," J. Med. Chem. 58(15):6179-6194.

"*Benzoic Acid Compounds, CAS Registry 1928308-82-0, 1928304-05-5; 1318973-99-7; 1317272-66-4; 1033194-63-6; 924823-28-9; and 518023-36-4*" (2022) 5 pages.

Appel, W.P.J. et al. (2014) "*Supramolecular Chemistry With Ureido-Benzoic Acids*," Chem. Sci. 5:3735-3745.

Baravkar, S.B. et al. (2017) "*Structural Insights into the Hydrogen-Bonding and Folding Pattern in Ant-Ant-Pro-Gly Tetrapeptides*," Eur. J. Org. Chem. 2017:2944-2949.

Bertrand, H. et al. (2013) "*Synthesis, Properties, and Remarkable 2D Self-Assembly at the Liquid/Solid Interface of a Series of Triskele-Shaped 5,11,17-Triazatrinaphthylenes (TrisK)*," Chem. Eur. J. 19:14654-14664.

CN201880063954.3; First Office Action (2022) 12 pages.

CN201880063954.3; Second Office Action (2023) 11 pages.

Huang, Y. et al. (2014) "*Palladium-Catalyzed Direct Ortho-C-H Ethoxycarboxylation of Anilides at Room Temperature*," Chem. Org. Front. 1:347-350.

Wang, S. et al. (2012) "*Efficient Synthesis of Anthranilic Esters via Pd-Catalyzed Dehydrogenative/Decarbonylative Coupling of Anilides and Glyoxylates*," Chem. Commun. 48:9924-9926.

EP Supp. Search Report EP 18843536.6 (2021) 13 pages.

\* cited by examiner (A)

(B)

(A)

Normal diet (B)

HFDT (C)

HFDT + H-77

(A) Normal diet (B) MCDD (C) MCDD + H-77

(A)

(B)

ANTHRANILIC ACID-BASED COMPOUND, AND PIN1 INHIBITOR, THERAPEUTIC AGENT FOR INFLAMMATORY DISEASES AND THERAPEUTIC AGENT FOR CANCER THAT USE THE SAME

CROSS-REFERENCE TO RELATED APPLICATIONS

This application is a § 371 Application of PCT/JP2018/029497 (filed on Aug. 6, 2018), which application claims priority to Japanese Patent Application 2017-152808 (filed on Aug. 7, 2017), each of which applications is incorporated herein by reference in its entirety and to which priority is claimed.

TECHNICAL FIELD

The present invention relates to new low-molecular-weight organic anthranilic acid-based compounds, and further relates to Pin1 inhibitors, pharmaceutical compositions, therapeutic or prophylactic agents for inflammatory diseases including non-alcoholic steatohepatitis (NASH), inflammatory bowel disease, and pulmonary fibrosis, for cancer, and for obesity, which are prepared using the compounds.

BACKGROUND ART

Pin1 is a kind of peptidyl-prolyl cis-trans isomerase (PPIase) that catalyzes cis/trans isomerization of proline residues in proteins, and is characterized in that the enzyme specifically acts on proline residues immediately preceded by phosphorylated serine or threonine to change the conformation of those proline residues. Accordingly, Pin1 is a molecule that couples phosphorylation of a protein to conformational change of the protein, and is considered to play an important role in intracellular signal transduction. In respect of Pin1, it is reported that Pin1 knockout mice manifest Alzheimer's-like pathology (Non-Patent Document 1), and that Pin1 inhibitors have ability to inhibit cancer cell growth (Non-Patent Documents 2 and 3).

Additionally, the inventors have previously reported that Pin1, a kind of cis-trans isomerase, associates with IRS-1, a protein playing a central role in insulin signaling, and enhances insulin signaling (Non-Patent Document 4).

As compounds that inhibit Pin1, a phenylalaninol-phosphate derivative, an indole- or benzimidazole-alanine derivative, a fredericamycin A compound, a phenyl-imidazole derivative, a naphthyl-substituted amino acid derivative, a glutamate or aspartate derivative, and the like have been reported (Patent Documents 1 to 4 and Non-Patent Documents 2, 3, 5, and 6).

The inventors previously found that use of Juglone, which is a compound known as a Pin1 inhibitor and having the following structure, and

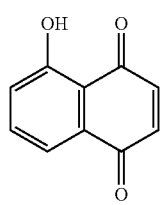 [SMILES: O=C1C=CC(=O)c2c(O)cccc21]

similarly use of (R)-2-(5-(4-methoxyphenyl)-2-methyl-furan-3-carboxamido)-3-(naphthalene-6-yl)propanoic acid (hereinafter referred to as C1), which is a compound known as a Pin1 inhibitor and having the following structure,

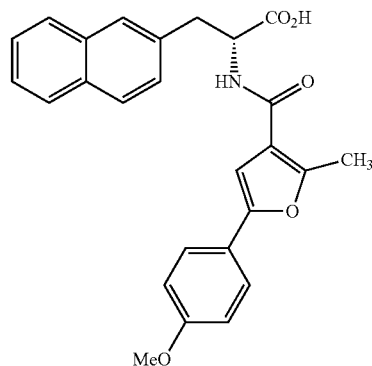 [SMILES: COc1ccc(-c2cc(C(=O)N[C@H](Cc3ccc4ccccc4c3)C(=O)O)c(C)o2)cc1]

resulted in prevention of colitis development in mice with induction of colitis and with oral administration of either of these Pin1 inhibitors (Non-Patent Document 7).

It is known that certain anthranilic acid-based compounds have an inhibitory activity against T-cell proliferation and are thus potentially used as therapeutic agents for diseases, such as autoimmune diseases (Patent Document 5).

PRIOR ART REFERENCES

Patent Documents

Patent Document 1: WO 2004/087720
Patent Document 2: WO 2006/040646
Patent Document 3: WO 2005/007123
Patent Document 4: WO 2002/060436
Patent Document 5: JP 2010-520857 T

Non-Patent Documents

Non-Patent Document 1: Yih-Cherng Liou, and 11 other authors, Nature, Published: Jul. 31, 2003, Vol. 424, pp. 556-561.
Non-Patent Document 2: Andrew Potter, and 16 other authors, Bioorganic & Medicinal Chemistry Letters (Bioorg. Med. Chem. Lett.), Published: Nov. 15, 2010 (Epub: Sep. 17, 2010), Vol. 20, No. 22, pp. 6483-6488.
Non-Patent Document 3: Andrew Potter, and 14 other authors, Bioorganic & Medicinal Chemistry Letters (Bioorg. Med. Chem. Lett.), Published: Jan. 15, 2010 (Epub: Nov. 22, 2009), Vol. 20, No. 2, pp. 586-590.
Non-Patent Document 4: Yusuke Nakatsu, Tomoichiro Asano, and 21 other authors, The Journal of Biological Chemistry (J. Biol. Chem.), Published: Jun. 10, 2011 (Epub: Mar. 17, 2011), Vol. 286, No. 23, pp. 20812-20822.
Non-Patent Document 5: Liming Dong, and 11 other authors, Bioorganic & Medicinal Chemistry Letters (Bioorg. Med. Chem. Lett.), Published: Apr. 1, 2010 (Epub: Feb. 14, 2010), Vol. 20, No. 7, pp. 2210-2214.
Non-Patent Document 6: Hidehiko Nakagawa, and 6 other authors, Bioorganic & Medicinal Chemistry Letters (Bioorg. Med. Chem. Lett.), Published: Dec. 1, 2015 (Epub: Oct. 22, 2015), Vol. 25, pp. 5619-5624.
Non-Patent Document 7: Tomoichiro Asano, "Novel treatment of inflammatory bowel diseases by Pin1 inhibitors", presentation for the DSANJ Biz Meeting Categorized by Target Diseases (gastrointestinal diseases) sponsored by the Osaka Chamber of Commerce and Industry, Published: Jan. 30, 2015.

DISCLOSURE OF THE INVENTION

Problems to be Solved by the Invention

In view of the current conditions as described above, an object of the present invention is to develop a group of new compounds with inhibitory activity against the function of Pin1 as candidate compounds for drugs.

Means for Solving the Problems

The inventors intensively studied to solve the above-described problem, and consequently developed a group of new compounds by synthesizing many anthranilic acid derivatives, each having an optionally substituted polycyclic aryl group, an optionally substituted polycyclic heterocyclic group, or a particular ring-assembly group, and found that these new compounds have a potential to be therapeutic agents for diseases, such as non-alcoholic steatohepatitis and cancer, as well as have an inhibitory activity against the function of Pin1, and finally completed the present invention.

That is, the present invention provides the following first invention relating to new compounds or salts thereof, the following second invention relating to Pin1 inhibitors, the following third invention relating to pharmaceutical compositions, the following fourth invention relating to therapeutic or prophylactic agents for inflammatory diseases associated with fibrosis including non-alcoholic steatohepatitis, inflammatory bowel disease, and pulmonary fibrosis, the following fifth invention relating to therapeutic or prophylactic agents for cancer, and the following sixth invention relating to therapeutic or prophylactic agents for obesity.

The first invention provides compounds represented by the following Formula (I), or salts thereof:

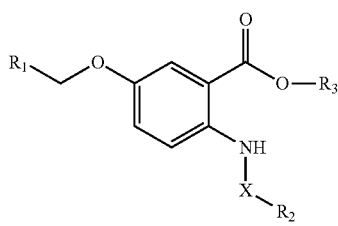

(I)

(wherein at least one of $R_1$ or $R_2$ represents an optionally substituted polycyclic aryl group, an optionally substituted polycyclic heterocyclic group, or a group represented by the following Formula (II):

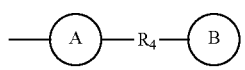

(II)

(wherein rings A and B independently represent an optionally substituted monocyclic or polycyclic aryl group, and $R_4$ represents an optionally substituted $C_{1-3}$ alkylene group, an optionally substituted $C_{2-3}$ alkenylene group, or a divalent oxy group);

either $R_1$ or $R_2$ represents, if not any of the above-described groups, a hydrogen atom, an optionally substituted hydrocarbon group, or an optionally substituted monocyclic heterocyclic group;

$R_3$ represents a hydrogen atom, an optionally substituted hydrocarbon group, or an optionally substituted heterocyclic group;

X represents a single bond, —CO— group, —CO—O—CH$_2$— group, —CO—CH$_2$—O— group, —SO$_2$— group, —CH$_2$—CO—NH— group, —CH$_2$—CO— group, or —CH$_2$— group).

In the compounds or salts thereof according to the first invention, at least one of $R_1$ or $R_2$ preferably represents an optionally substituted polycyclic aryl group.

In this case, at least one of $R_1$ or $R_2$ more preferably represents an optionally substituted naphthyl group.

Further preferably, $R_1$ represents an optionally substituted naphthyl group.

In any aforementioned compound or a salt thereof, $R_3$ preferably represents a hydrogen atom or a methyl group.

In any aforementioned compound or a salt thereof, X preferably represents a —CO— group.

The second invention provides Pin1 inhibitors comprising any aforementioned compound or a salt thereof.

The third invention provides pharmaceutical compositions comprising any aforementioned compound or a pharmaceutically acceptable salt thereof and a pharmaceutically acceptable carrier.

The fourth invention provides therapeutic or prophylactic agents for inflammatory diseases associated with fibrosis, which comprise a compound represented by following Formula (I) or a pharmaceutically acceptable salt thereof as an active ingredient:

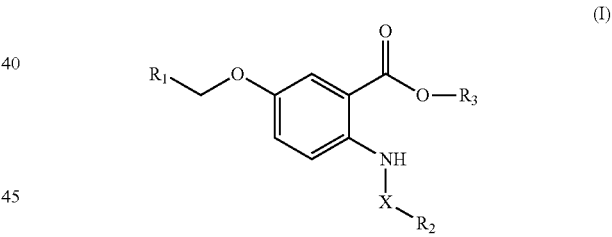

(I)

(wherein at least one of $R_1$ or $R_2$ represents an optionally substituted polycyclic aryl group, an optionally substituted polycyclic heterocyclic group, or a group represented by the following Formula (II):

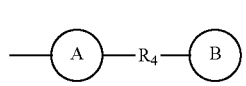

(II)

(wherein rings A and B independently represent an optionally substituted monocyclic or polycyclic aryl group, and $R_4$ represents an optionally substituted $C_{1-3}$ alkylene group, an optionally substituted $C_{2-3}$ alkenylene group, or a divalent oxy group);

either $R_1$ or $R_2$, if not any of the above-described groups, represents a hydrogen atom, an optionally substituted hydrocarbon group, or an optionally substituted monocyclic heterocyclic group;

R₃ represents a hydrogen atom, an optionally substituted hydrocarbon group, or an optionally substituted heterocyclic group;

X represents a single bond, —CO— group, —CO—O—CH₂— group, —CO—CH₂—O— group, —SO₂— group, —CH₂—CO—NH— group, —CH₂—CO— group, or —CH₂— group).

In respect of the therapeutic or prophylactic agents for inflammatory diseases associated with fibrosis according to the fourth invention, the inflammatory diseases associated with fibrosis are non-alcoholic steatohepatitis, inflammatory bowel disease, and pulmonary fibrosis.

In any aforementioned therapeutic or prophylactic agent for an inflammatory disease associated with fibrosis, at least one of R₁ or R₂ preferably represents an optionally substituted polycyclic aryl group.

In this case, at least one of R₁ or R₂ more preferably represents an optionally substituted naphthyl group.

Further preferably, R₁ represents an optionally substituted naphthyl group.

In any aforementioned therapeutic or prophylactic agent for an inflammatory disease associated with fibrosis, R₃ preferably represents a hydrogen atom or a methyl group.

In any aforementioned therapeutic or prophylactic agent for an inflammatory disease associated with fibrosis, X preferably represents a —CO— group.

Any aforementioned therapeutic or prophylactic agent for an inflammatory disease associated with fibrosis may further comprise active ingredients in at least one or more drugs selected from the group of other therapeutic or prophylactic agents for the inflammatory disease associated with fibrosis.

Moreover, any aforementioned therapeutic or prophylactic agent for an inflammatory disease associated with fibrosis may be used in combination with at least one or more drugs selected from the group of other therapeutic or prophylactic agents for the inflammatory disease associated with fibrosis.

The fourth invention provides any aforementioned compound or a pharmaceutically acceptable salt thereof for use as a therapeutic or prophylactic agent for an inflammatory disease associated with fibrosis.

The fourth invention also provides use of any aforementioned compound or a pharmaceutically acceptable salt thereof for the manufacture of a medicament for the treatment or prevention of an inflammatory disease associated with fibrosis.

Moreover, the fourth invention also provides a method of treating or preventing an inflammatory disease associated with fibrosis by administering any aforementioned compound or a pharmaceutically acceptable salt thereof to a patient.

The fifth invention provides therapeutic or prophylactic agents for cancer, which comprise a compound represented by following Formula (I) or a pharmaceutically acceptable salt thereof as an active ingredient:

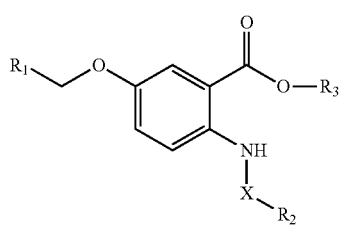

(I)

(wherein at least one of R₁ or R₂ represents an optionally substituted polycyclic aryl group, an optionally substituted polycyclic heterocyclic group, or a group represented by the following Formula (II):

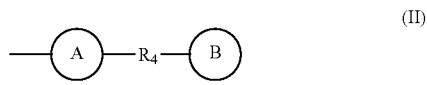

(II)

(wherein rings A and B independently represent an optionally substituted monocyclic or polycyclic aryl group, and R₄ represents an optionally substituted C₁₋₃ alkylene group, an optionally substituted C₂₋₃ alkenylene group, or a divalent oxy group);

either R₁ or R₂ represents, if not any of the above-described groups, a hydrogen atom, an optionally substituted hydrocarbon group, or an optionally substituted monocyclic heterocyclic group;

R₃ represents a hydrogen atom, an optionally substituted hydrocarbon group, or an optionally substituted heterocyclic group;

X represents a single bond, —CO— group, —CO—O—CH₂— group, —CO—CH₂—O— group, —SO₂— group, —CH₂—CO—NH— group, —CH₂—CO— group, or —CH₂— group).

The therapeutic or prophylactic agents for cancer according to the fifth invention can be suitably used when the cancer is colon cancer or prostate cancer.

In any aforementioned therapeutic or prophylactic agent for cancer, at least one of R₁ or R₂ preferably represents an optionally substituted polycyclic aryl group.

In this case, at least one of R₁ or R₂ more preferably represents an optionally substituted naphthyl group.

Further preferably, R₁ represents an optionally substituted naphthyl group.

In any aforementioned therapeutic or prophylactic agent for cancer, R₃ preferably represents a hydrogen atom or a methyl group.

In any aforementioned therapeutic or prophylactic agent for cancer, X preferably represents a —CO— group.

Any aforementioned therapeutic or prophylactic agent for cancer may further comprise active ingredients in at least one or more drugs selected from the group of other therapeutic or prophylactic agents for cancer.

Moreover, any aforementioned therapeutic or prophylactic agent for cancer may be used in combination with at least one or more drugs selected from the group of other therapeutic or prophylactic agents for cancer.

The fifth invention provides any aforementioned compound or a pharmaceutically acceptable salt thereof for use as a therapeutic or prophylactic agent for cancer.

The fifth invention also provides use of any aforementioned compound or a pharmaceutically acceptable salt thereof for the manufacture of a medicament for the treatment or prevention of cancer.

Moreover, the fifth invention also provides a method of treating or preventing cancer by administering any aforementioned compound or a pharmaceutically acceptable salt thereof to a patient.

The sixth invention provides therapeutic or prophylactic agents for obesity, which comprise a compound represented by following Formula (I) or a pharmaceutically acceptable salt thereof as an active ingredient:

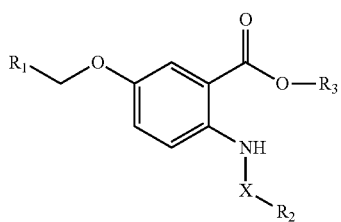

(wherein at least one of $R_1$ or $R_2$ represents an optionally substituted polycyclic aryl group, an optionally substituted polycyclic heterocyclic group, or a group represented by the following Formula (II):

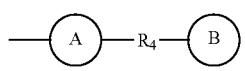

(wherein rings A and B independently represent an optionally substituted monocyclic or polycyclic aryl group, and $R_4$ represents an optionally substituted $C_{1-3}$ alkylene group, an optionally substituted $C_{2-3}$ alkenylene group, or a divalent oxy group);

either $R_1$ or $R_2$ represents, if not any of the above-described groups, a hydrogen atom, an optionally substituted hydrocarbon group, or an optionally substituted monocyclic heterocyclic group;

$R_3$ represents a hydrogen atom, an optionally substituted hydrocarbon group, or an optionally substituted heterocyclic group;

X represents a single bond, —CO— group, —CO—O—$CH_2$— group, —CO—$CH_2$—O— group, —$SO_2$— group, —$CH_2$—CO—NH— group, —$CH_2$—CO— group, or —$CH_2$— group).

In the therapeutic or prophylactic agents for obesity according to the sixth invention, at least one of $R_1$ or $R_2$ preferably represents an optionally substituted polycyclic aryl group.

In this case, at least one of $R_1$ or $R_2$ more preferably represents an optionally substituted naphthyl group.

Further preferably, $R_1$ represents an optionally substituted naphthyl group.

In any aforementioned therapeutic or prophylactic agent for obesity, $R_3$ preferably represents a hydrogen atom or a methyl group.

In any aforementioned therapeutic or prophylactic agent for obesity, X preferably represents a —CO— group.

Any aforementioned therapeutic or prophylactic agent for obesity may further comprise active ingredients in at least one or more drugs selected from the group of other therapeutic or prophylactic agents for obesity.

Moreover, any aforementioned therapeutic or prophylactic agent for obesity may be used in combination with at least one or more drugs selected from the group of other therapeutic or prophylactic agents for obesity.

The sixth invention provides any aforementioned compound or a pharmaceutically acceptable salt thereof for use as a therapeutic or prophylactic agent for obesity.

The sixth invention also provides use of any aforementioned compound or a pharmaceutically acceptable salt thereof for the manufacture of a medicament for the treatment or prevention of obesity.

Moreover, the sixth invention also provides a method of treating or preventing obesity by administering any aforementioned compound or a pharmaceutically acceptable salt thereof to a patient.

Effect of the Invention

Any new compound or a salt thereof according to the first invention is a compound with inhibitory activity against the function of Pin1, or a precursor thereof, or becomes a therapeutic or prophylactic agent or a prodrug thereof for, for example, non-alcoholic steatohepatitis or cancer, and therefore can be effectively used for development of a Pin1 inhibitor or a drug used for inflammatory diseases or cancer.

Any Pin1 inhibitor according to the second invention exerts an inhibitory activity against the function of Pin1.

Pharmaceutical compositions according to the third invention have an effect based on inhibition of Pin1 function as a mechanism of action to treat or prevent diseases.

Therapeutic or prophylactic agents for inflammatory diseases associated with fibrosis according to the fourth invention have an effect to alleviate the conditions of inflammatory diseases associated with fibrosis, such as non-alcoholic steatohepatitis, inflammatory bowel disease, and pulmonary fibrosis, or to prevent development of inflammatory diseases associated with fibrosis.

Therapeutic or prophylactic agents for cancer according to the fifth invention have an effect to inhibit cancer growth or an effect to prevent cancer development.

Therapeutic or prophylactic agents for obesity according to the sixth invention have an effect to reduce accumulation of body fat and thereby to treat or prevent obesity.

BRIEF DESCRIPTION OF THE DRAWINGS

FIG. 1 (A) is a graph depicting the result of measurement of mouse liver weight, and FIG. 1 (B) is a graph depicting the result of measurement of blood AST (GOT) concentration in mice. In FIGS. 1 (A) and (B), graph bars represent the measurement results in control mice, NASH mice given a HFDT, NASH mice given a HFDT and H-77, and NASH mice given a HFDT and Juglone, from left to right.

FIG. 2 (A) is a photograph depicting the result of observation of liver tissue from control mice given a normal diet, and FIG. 2 (B) is a photograph depicting the result of observation of liver tissue from NASH mice given a HFDT, and FIG. 2 (C) is a photograph depicting the result of observation of liver tissue from NASH mice given a HFDT and H-77.

FIG. 3 (A) is a photograph depicting the result of observation of liver tissue from control mice given a normal diet, and FIG. 3 (B) is a photograph depicting the result of observation of liver tissue from NASH mice given a MCDD, and FIG. 3 (C) is a photograph depicting the result of observation of liver tissue from NASH mice given a MCDD and H-77.

FIG. 4 (A) illustrates the distribution of tumor volume ratio (%) in the first tumor at 9 weeks after administration of a compound, where the tumor volume at the beginning of the administration is set as 100, and shows the distribution of size change in control mice and mice given H-77, from left to right, expressed in box plot. FIG. 4 (B) illustrates the distribution of volume of the second tumor and shows the distribution of tumor volume in control mice and mice given H-77, from left to right, expressed in box plot.

DESCRIPTION OF EMBODIMENTS

Figure 1:
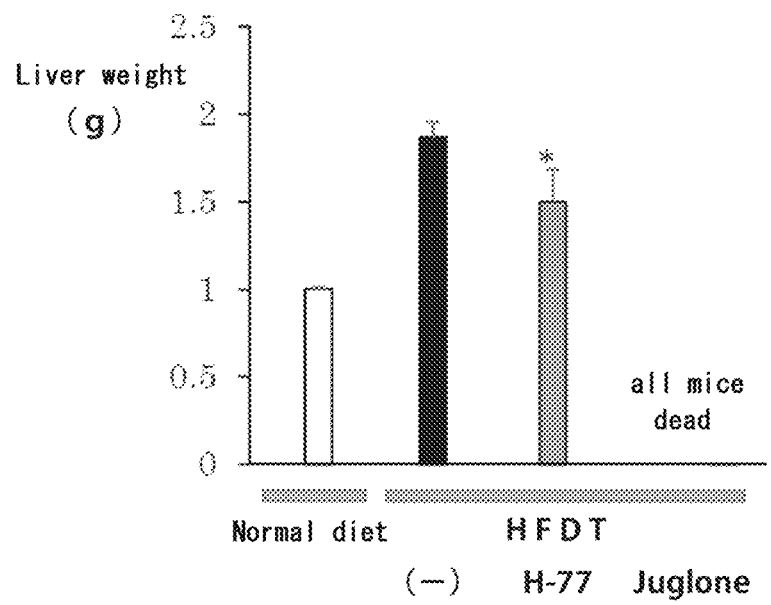
FIG. 1 shows graphs depicting results of measurements of liver weight change and blood AST (GOT) concentration in mice in a NASH treatment study.
Figure 1:
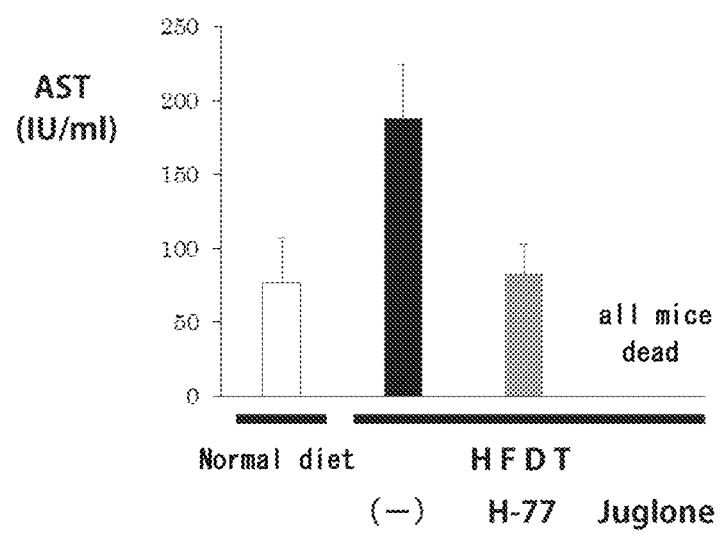

1. Compounds or Salts Thereof
1-1. Structure of Compounds

A compound according to the present invention has a chemical structure represented by the following Formula (I).

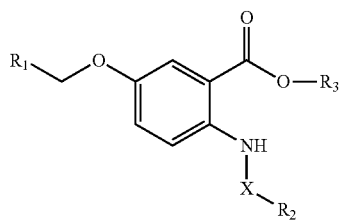
(I)

In the Formula (I), at least one of $R_1$ or $R_2$ represents an optionally substituted polycyclic aryl group, an optionally substituted polycyclic heterocyclic group, or a group represented by the following Formula (II):

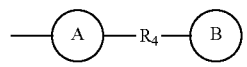
(II)

(wherein rings A and B independently represent an optionally substituted monocyclic or polycyclic aryl group, and $R_4$ represents an optionally substituted $C_{1-3}$ alkylene group, an optionally substituted $C_{2-3}$ alkenylene group, or a divalent oxy group).

If either $R_1$ or $R_2$ does not represents any of the above-described groups, namely, an optionally substituted polycyclic aryl group, an optionally substituted polycyclic heterocyclic group, and a group represented by the above Formula (II), either $R_1$ or $R_2$ represents a hydrogen atom, an optionally substituted hydrocarbon group (excluding optionally substituted polycyclic aryl groups), or an optionally substituted monocyclic heterocyclic group.

In the Formula (I), "at least one of $R_1$ or $R_2$" means both "$R_1$ or $R_2$" and "$R_1$ and $R_2$."

Thus, in cases where $R_1$ represents an optionally substituted polycyclic aryl group, an optionally substituted polycyclic heterocyclic group, or a group represented by the above Formula (II), $R_2$ may be or may not be any of the above groups. That is, in this case, $R_2$ may be a hydrogen atom, an optionally substituted hydrocarbon group (excluding optionally substituted polycyclic aryl groups), or an optionally substituted monocyclic heterocyclic group, or may be an optionally substituted polycyclic aryl group, an optionally substituted polycyclic heterocyclic group, or a group represented by the above Formula (II).

Similarly, in cases where $R_2$ represents an optionally substituted polycyclic aryl group, an optionally substituted polycyclic heterocyclic group, or a group represented by the above Formula (II), $R_1$ may be or may not be any of the above groups. That is, In this case, $R_1$ may be a hydrogen atom, an optionally substituted hydrocarbon group (excluding optionally substituted polycyclic aryl groups), or an optionally substituted monocyclic heterocyclic group, or may be an optionally substituted polycyclic aryl group, an optionally substituted polycyclic heterocyclic group, or a group represented by the above Formula (II).

In the above Formula (I), at least one of $R_1$ or $R_2$ represents an optionally substituted polycyclic aryl group, an optionally substituted polycyclic heterocyclic group, or a group represented by the above Formula (II), and preferably represents an optionally substituted polycyclic aryl group or an optionally substituted polycyclic heterocyclic group to enhance the inhibitory activity against the function of Pin1. Either $R_1$ or $R_2$ more preferably represents an optionally substituted polycyclic aryl group and further preferably represents a polycyclic aryl group.

In the above Formula (I), at least one of $R_1$ or $R_2$ can represent an optionally substituted polycyclic aryl group. In the present invention, the "polycyclic aryl group" refers to a group derived from an aromatic compound including a condensed ring system with two or more carbocycles.

In this respect, a bicyclic to tetracyclic aryl group is preferably used as the "polycyclic aryl group."

Examples of the "polycyclic aryl group" in the present invention can include, but are not limited to, indenyl group, naphthyl group, fluorenyl group, anthryl group, biphenylenyl group, phenanthrenyl group, as-indacenyl group, s-indacenyl group, acenaphthylenyl group, phenalenyl group, fluoranthenyl group, pyrenyl group, naphthacenyl group, and hexacenyl group.

The chemical structure of the "optionally substituted polycyclic aryl group" in the present invention can be specifically illustrated by, but not limited to, those of the following groups.

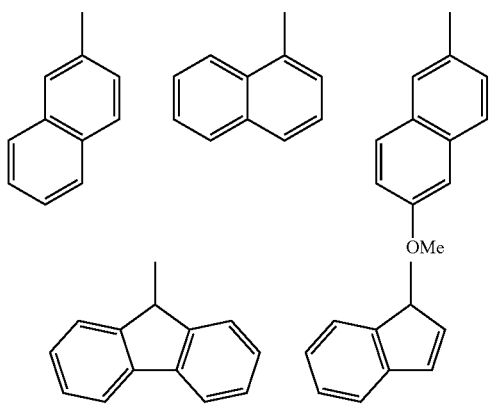

In the present invention, the "optionally substituted polycyclic aryl group" is preferably an optionally substituted naphthyl group. In this respect, the optionally substituted naphthyl group may be attached to the main structure of a compound represented by the Formula (I) at position 1 or 2 of the naphthyl group.

Such "optionally substituted naphthyl groups" can be represented by the following Formula (III).

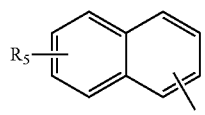

(III)

In the Formula (III), R$_5$ represents 0 to 7 identical or different substituents attached to the naphthyl group. R$_5$ may be attached to the naphthyl group at any of positions 1 through 8. However, R$_5$ is not allowed to be attached to the naphthyl group where the main structure of the compound is attached. In addition, R$_5$ may also be unattached to the naphthyl group, which results in formation of an unsubstituted naphthyl group. In cases where R$_5$ is attached to the naphthyl group, the number of R$_5$ can be from 1 to 7, and the substituents represented by R$_5$ may be different from each other or be wholly or partly identical. R$_5$ is preferably a substituent containing 1 to 10 atoms.

In the above Formula (I), at least one of R$_1$ or R$_2$ can represent an optionally substituted polycyclic heterocyclic group. In the present invention, the "polycyclic heterocyclic group" refers to a group including a condensed ring system with two or more rings composed of atoms of carbon and some other elements.

As the "polycyclic heterocyclic group," an aromatic heterocyclic group is preferably used.

The "polycyclic heterocyclic group" in the present invention can be, but is not limited to, for example, 5- to 14-membered bicyclic to pentacyclic heterocyclic groups each having carbon atoms and further having one to four heteroatoms of one or two elements selected from nitrogen, oxygen, and sulfur. Specific examples of the polycyclic heterocyclic group can include, but not limited to, bicyclic to tetracyclic condensed ring groups each having carbon atoms and further having one to four heteroatoms selected from oxygen, sulfur, and nitrogen, such as indolyl group, benzofuryl group, benzothiazolyl group, benzoxazolyl group, xanthenyl group, benzimidazolyl group, quinolyl group, isoquinolyl group, phthalazinyl group, quinazolinyl group, quinoxalinyl group, indolizinyl group, quinolizinyl group, 1,8-naphthyridinyl group, dibenzofuranyl group, carbazolyl group, acridinyl group, phenanthridinyl group, perimidinyl group, phenazinyl group, chromanyl group, phenothiazinyl group, phenoxazinyl group, and 7H-pirazino[2,3-c]carbazolyl group.

The chemical structure of the "optionally substituted polycyclic heterocyclic group" in the present invention can be specifically illustrated by, but not limited to, those of the following groups.

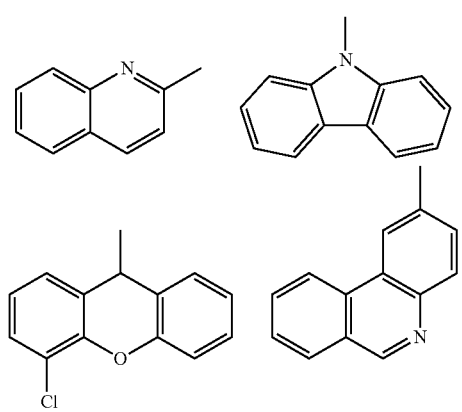

In the above Formula (I), at least one of R$_1$ or R$_2$ can represent a group represented by the following Formula (II):

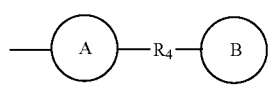

(II)

(wherein rings A and B independently represent an optionally substituted monocyclic or polycyclic aryl group, and R$_4$ represents an optionally substituted C$_{1-3}$ alkylene group, an optionally substituted C$_{2-3}$ alkenylene group, or a divalent oxy group).

In the present invention, examples of the "monocyclic or polycyclic aryl group" can include, but are not limited to, phenyl group, indenyl group, naphthyl group, fluorenyl group, anthryl group, biphenylenyl group, phenanthrenyl group, as-indacenyl group, s-indacenyl group, acenaphthylenyl group, phenalenyl group, fluoranthenyl group, pyrenyl group, naphthacenyl group, and hexacenyl group.

In the present invention, examples of the "C$_{1-3}$ alkylene group" can include, but are not limited to, methylene group, ethylene group, and trimethylene group.

Moreover, examples of the "C$_{2-3}$ alkenylene group" in the present invention can include, but are not limited to, vinylene group, 1-propenylene group, and 2-propenylene group.

In the above Formula (II), R$_4$ can represent a divalent oxy group. In this case, the above Formula (II) can be represented by the following Formula (IV):

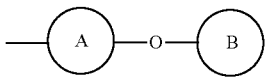

(IV)

(wherein rings A and B independently represent an optionally substituted monocyclic or polycyclic aryl group).

In the above Formula (I), either R$_1$ or R$_2$ should represent a hydrogen atom, an optionally substituted hydrocarbon group (excluding optionally substituted polycyclic aryl groups), or an optionally substituted monocyclic heterocyclic group, preferably a hydrogen atom or an optionally substituted phenyl group, if it is not an optionally substituted polycyclic aryl group, an optionally substituted polycyclic heterocyclic group, or a group represented by the Formula (II).

In the present invention, the "hydrocarbon group" means a group derived from a compound composed of carbon and hydrogen atoms. Examples of the hydrocarbon group can include, but are not limited to, aliphatic hydrocarbon, monocyclic saturated hydrocarbon, and aromatic hydrocarbon groups, and preferably contain 1 to 16 carbon atoms. Specific examples of the hydrocarbon group include, but are not limited to, alkyl groups, alkenyl groups, alkynyl groups, cycloalkyl groups, and aryl groups.

In this respect, examples of "alkyl group" include methyl group, ethyl group, propyl group, isopropyl group, butyl group, isobutyl group, sec-butyl group, tert-butyl group, pentyl group, and hexyl group. Examples of "alkenyl group" include vinyl group, 1-propenyl group, allyl group, isopropenyl group, butenyl group, and isobutenyl group. Examples of "alkynyl group" include ethynyl group, propargyl group, and 1-propynyl group. Examples of "cycloalkyl group"

include cyclopropyl group, cyclobutyl group, cyclopentyl group, and cyclohexyl group. Examples of "aryl group" include phenyl group, indenyl group, naphthyl group, fluorenyl group, anthryl group, biphenylenyl group, phenanthrenyl group, as-indacenyl group, s-indacenyl group, acenaphthylenyl group, phenalenyl group, fluoranthenyl group, pyrenyl group, naphthacenyl group, and hexacenyl group.

In the present invention, examples of the "monocyclic heterocyclic group" can include, but are not limited to, 5-membered heterocyclic groups each having carbon atoms and further having one to four heteroatoms selected from oxygen, sulfur, and nitrogen, such as 2- or 3-thienyl group, 2- or 3-furyl group, 1-, 2- or 3-pyrrolyl group, 1-, 2- or 3-pyrrolidinyl group, 2-, 4- or 5-oxazolyl group, 3-, 4- or 5-isooxazolyl group, 2-, 4- or 5-thiazolyl group, 3-, 4- or 5-isothiazolyl group, 3-, 4- or 5-pyrazolyl group, 2-, 3- or 4-pyrazolidinyl group, 2-, 4- or 5-imidazolyl group, 1,2,3-triazolyl group, 1,2,4-triazolyl group, and 1H- or 2H-tetrazolyl group. Moreover, specific examples of the monocyclic heterocyclic group can include 6-membered cyclic groups each having carbon atoms and further having one to four heteroatoms selected from oxygen, sulfur, and nitrogen, such as 2-, 3- or 4-pyridyl group, N-oxide-2-, 3- or 4-pyridyl group, 2-, 4- or 5-pyrimidinyl group, N-oxide-2-, 4- or 5-pyrimidinyl group, thiomorpholinyl group, morpholinyl group, piperidino group, 2-, 3- or 4-piperidyl group, thiopyranyl group, 1,4-oxazinyl group, 1,4-thiazinyl group, 1,3-thiazinyl group, piperazinyl group, triazinyl group, 3- or 4-pyridazinyl group, pyrazinyl group, and N-oxide-3- or 4-pyridazinyl group.

In the above Formula (I), $R_3$ represents a hydrogen atom, an optionally substituted hydrocarbon group, or an optionally substituted heterocyclic group. $R_3$ preferably represents a hydrogen atom or a methyl group, more preferably a hydrogen atom.

In cases where $R_3$ represents a hydrogen atom to form a carboxyl group, the resultant compound according to the present invention has high activity. However, even if $R_3$ does not represents a hydrogen atom and an ester is formed, hydrolysis of the ester can easily produce a carboxyl group and the resultant compound can have high activity. Thus, in cases where $R_3$ represents an optionally substituted hydrocarbon group or an optionally substituted heterocyclic group, the compound according to the present invention can be used as a prodrug.

In the present invention, the "heterocyclic group" refers to a group derived from a cyclic compound composed of atoms of carbon and some other elements. As the "heterocyclic group," an aromatic heterocyclic group is preferably used.

In the present invention, the "heterocyclic group" can be, but is not limited to, for example, any of 5- to 14-membered monocyclic to pentacyclic heterocyclic groups each having carbon atoms and further having one to four heteroatoms of one or two elements selected from nitrogen, oxygen, and sulfur. Specific examples of the heterocyclic group can include, but are not limited to, 5-membered cyclic groups each having carbon atoms and further having one to four heteroatoms selected from oxygen, sulfur, and nitrogen, such as 2- or 3-thienyl group, 2- or 3-furyl group, 1-, 2- or 3-pyrrolyl group, 1-, 2- or 3-pyrrolidinyl group, 2-, 4- or 5-oxazolyl group, 3-, 4- or 5-isooxazolyl group, 2-, 4- or 5-thiazolyl group, 3-, 4- or 5-isothiazolyl group, 3-, 4- or 5-pyrazolyl group, 2-, 3- or 4-pyrazolidinyl group, 2-, 4- or 5-imidazolyl group, 1,2,3-triazolyl group, 1,2,4-triazolyl group, and 1H- or 2H-tetrazolyl group. Moreover, specific examples of the heterocyclic group can include 6-membered cyclic groups each having carbon atoms and further having one to four heteroatoms selected from oxygen, sulfur, and nitrogen, such as 2-, 3- or 4-pyridyl group, N-oxide-2-, 3- or 4-pyridyl group, 2-, 4- or 5-pyrimidinyl group, N-oxide-2-, 4- or 5-pyrimidinyl group, thiomorpholinyl group, morpholinyl group, piperidino group, 2-, 3- or 4-piperidyl group, thiopyranyl group, 1,4-oxazinyl group, 1,4-thiazinyl group, 1,3-thiazinyl group, piperazinyl group, triazinyl group, 3- or 4-pyridazinyl group, pyrazinyl group, and N-oxide-3- or 4-pyridazinyl group. Moreover, specific examples of the heterocyclic group can include bicyclic to tetracyclic condensed ring groups each having carbon atoms and further having one to four heteroatoms selected from oxygen, sulfur, and nitrogen, such as indolyl group, benzofuryl group, benzothiazolyl group, benzoxazolyl group, xanthenyl group, benzimidazolyl group, quinolyl group, isoquinolyl group, phthalazinyl group, quinazolinyl group, quinoxalinyl group, indolizinyl group, quinolizinyl group, 1,8-naphthyridinyl group, dibenzofuranyl group, carbazolyl group, acridinyl group, phenanthridinyl group, perimidinyl group, phenazinyl group, chromanyl group, phenothiazinyl group, phenoxazinyl group, and 7H-pirazino[2,3-c]carbazolyl group.

In the above Formula (I), X represents a single bond, —CO— group, —CO—O—CH$_2$— group, —CO—CH$_2$—O— group, —SO$_2$— group, —CH$_2$—CO—NH— group, —CH$_2$—CO— group, or —CH$_2$— group.

X preferably represents a single bond or a —CO— group (carbonyl group).

In cases where X represents a single bond, the above Formula (I) can alternatively be illustrated by the following Formula (V):

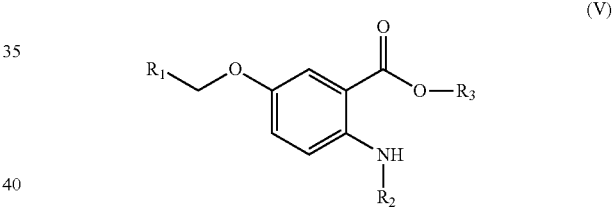

(wherein $R_1$, $R_2$, and $R_3$ are the same as defined above).

The "substituent" as used in the present invention is a halogen (such as, for example, fluorine, chlorine, bromine, or iodine), an alkyl group (for example, a $C_{1-6}$ alkyl group, such as methyl group, ethyl group, propyl group, isopropyl group, butyl group, isobutyl group, sec-butyl group, tert-butyl group, pentyl group, or hexyl group), a cycloalkyl group (for example, a $C_{3-6}$ cycloalkyl group, such as cyclopropyl group, cyclobutyl group, cyclopentyl group, or cyclohexyl group), an alkynyl group (for example, a $C_{2-6}$ alkynyl group, such as ethynyl group, 1-propynyl group, or propargyl group), an alkenyl group (for example, a $C_{2-6}$ alkenyl group, such as vinyl group, allyl group, isopropenyl group, butenyl group, or isobutenyl group), an aralkyl group (for example, a $C_{7-11}$ aralkyl group, such as benzyl group, α-methylbenzyl group, or phenethyl group), an aryl group (for example, a $C_{6-10}$ aryl group, such as phenyl group or naphthyl group; preferably phenyl group), an alkoxy group (for example, a $C_{1-6}$ alkoxy group, such as methoxy group, ethoxy group, propoxy group, isopropoxy group, butoxy group, isobutoxy group, sec-butoxy group, or tert-butoxy), an aryloxy group (for example, a $C_{6-10}$ aryloxy group, such as phenoxy), an alkanoyl group (for example, a $C_{1-6}$ alkylcarbonyl group, such as formyl group, acetyl group, propionyl group, butyryl group, or isobutyryl group), an arylcarbonyl group (for example, a $C_{6-10}$ aryl-carbonyl group, such as benzoyl group or naphthoyl group), an alkanoyloxy group (for example, a $C_{1-6}$ alkyl-carbonyloxy group, such as formyloxy group, acetyloxy group, propionyloxy group, butyryloxy group, or isobutyryloxy group), an arylcarbonyloxy group (for example, a $C_{6-10}$ aryl-carbonyloxy group, such as benzoyloxy group or naphthoyloxy group), carboxyl group, an alkoxycarbonyl group (for example, a $C_{1-6}$ alkoxycarbonyl group, such as methoxycarbonyl group, ethoxycarbonyl group, propoxycarbonyl group, isopropoxycarbonyl group, butoxycarbonyl group, isobutoxycarbonyl group, or tert-butoxycarbonyl), an aralkyloxycarbonyl group (for example, a $C_{7-11}$ aralkyloxycarbonyl group, such as benzyloxycarbonyl group), carbamoyl group, a halogenated alkyl group (for example, a mono-, di-, or tri-halogenated —$C_{1-4}$ alkyl group, such as chloromethyl group, dichloromethyl group, trifluoromethyl group, or 2,2,2-trifluoroethyl group), oxo group, amidino group, imino group, amino group, an alkylamino group (for example, a mono-$C_{1-4}$ alkylamino group, such as methylamino group, ethylamino group, propylamino group, isopropylamino group, or butylamino group), a dialkylamino group (for example, a di-$C_{1-4}$ alkylamino group, such as dimethylamino group, diethylamino group, dipropylamino group, diisopropylamino group, dibutylamino group, or methylethylamino group), an alkoxycarbonylamino group (for example, a $C_{1-6}$ alkoxycarbonylamino group, such as methoxycarbonylamino group, isoproxycarbonylamino group, or tert-butoxycarbonylamino group), a cyclic amino group (a 3- to 6-membered cyclic amino group containing carbon atoms and one nitrogen atom and further containing one to three heteroatoms selected from oxygen, sulfur, and nitrogen; such as, for example, aziridinyl group, azetidinyl group, pyrrolidinyl group, pyrrolinyl group, pyrrolyl group, imidazolyl group, pyrazolyl group, imidazolidinyl group, piperidyl group, morpholinyl group, dihydropyridyl group, pyridyl group, N-methylpiperazinyl group, or N-ethylpiperazinyl group), alkylenedioxy group (for example, a $C_{1-3}$ alkylenedioxy group, such as methylenedioxy group or ethylenedioxy group), hydroxy group, cyano group, mercapto group, sulfo group, sulfino group, phosphono group, sulfamoyl group, a monoalkylsulfamoyl group (for example, a mono-$C_{1-6}$ alkylsulfamoyl group, such as N-methylsulfamoyl, N-ethylsulfamoyl, N-propylsulfamoyl, N-isopropylsulfamoyl, or N-butylsulfamoyl), a dialkylsulfamoyl group (for example, a di-$C_{1-6}$ alkylsulfamoyl group, such as N,N-dimethylsulfamoyl group, N,N-diethylsulfamoyl group, N,N-dipropylsulfamoyl group, or N,N-dibutylsulfamoyl group), an alkylthio group (for example, a $C_{1-6}$ alkylthio group, such as methylthio group, ethylthio group, propylthio group, isopropylthio group, butylthio group, sec-butylthio group, or tert-butylthio group), an arylthio group (for example, a $C_{6-10}$ arylthio group, such as phenylthio group or naphthylthio group), an alkylsulfinyl group (for example, a $C_{1-6}$ alkylsulfinyl group, such as methylsulfinyl group, ethylsulfinyl group, propylsulfinyl group, or butylsulfinyl group), an alkylsulfonyl group (for example, a $C_{1-6}$ alkylsulfonyl group, such as methylsulfonyl group, ethylsulfonyl group, propylsulfonyl group, or butylsulfonyl group), or an arylsulfonyl group (for example, a $C_{6-10}$ arylsulfonyl group, such as phenylsulfonyl group or naphthylsulfonyl group).

In the present invention, the "substituent containing 1 to 10 atoms" used for $R_5$ includes substituents containing 1 to 10 atoms selected from the above-described substituents, and examples of such substituent include, but are not limited to, halogens, methyl group, ethyl group, vinyl group, methoxy group, ethoxy group, acetyl group, carboxyl group, methoxycarbonyl group, chloromethyl group, amino group, methylamino group, hydroxy group, sulfo group, and methylthio group.

In the present invention, the phrase "optionally substituted" means that a substituent as described above is present or absent. In cases where a moiety is substituted, two or more substituents may be present within the moiety, and the substituents may be identical to or different from each other. In cases where a compound according to the present invention is "optionally substituted," the number of substituents within the compound is preferably from 0 to 3.

1-2. Salts of Compounds

A salt of a compound according to the present invention may be a salt with, for example, an inorganic or organic base, an inorganic or organic acid, or an acidic or basic amino acid. In cases where a compound represented by the Formula (I) according to the present invention has an acidic functional group, a salt of the compound can be formed with an inorganic base, an organic base, or a basic amino acid. Additionally, in cases where a compound represented by the Formula (I) according to the present invention has a basic functional group, a salt of the compound can be formed with an inorganic acid, an organic acid, or an acidic amino acid.

Examples of the salt with an inorganic base include, but are not limited to, sodium, potassium, and ammonium salts. Examples of the salt with an organic base include, but are not limited to, trimethylamine, ethanolamine, and cyclohexylamine salts. Examples of the salt with an inorganic acid include, but are not limited to, hydrochloride and phosphate salts. Examples of the salt with an organic acid include, but are not limited to, acetate, phthalate, fumarate, and oxalate salts. Examples of the salt with an acidic amino acid include, but are not limited to, salts with aspartic acid and with glutamic acid, while examples of the salt with a basic amino acid include salts with arginine and with lysine.

1-3. Methods for Compound Production

A compound according to the present invention can be synthesized by, for example, but not limited to, using an anthranilic acid derivative represented by the following Formula (VI), according to the scheme shown in the following reaction flow chart, which anthranilic acid derivative is synthesized from anthranilic acid as a starting material according to the reaction described in J. Org. Chem., 2001, vol. 66, pp. 2784-2788:

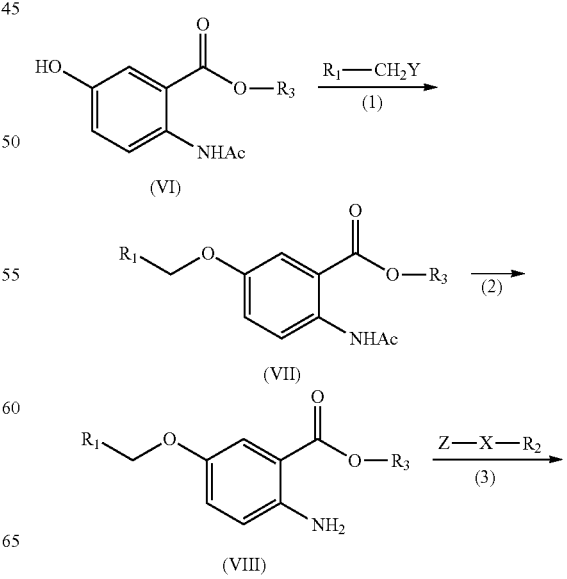

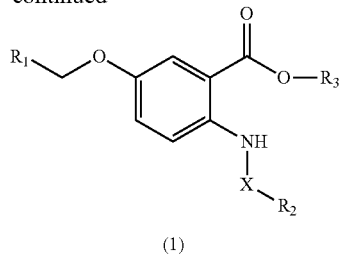

(wherein $R_1$, $R_2$, $R_3$, and X are the same as defined above, and Y represents a halogen atom, and Z can be a halogen atom, or may be a —OH group when the adjacent X represents a —CO— (acyl group)).

In the above scheme, the reaction (1) is a reaction for etherifying a hydroxy group, which can be performed in the presence of a base and an alkyl halide. Additionally, the reaction (2) is a reaction for removing an acetyl group, which can be performed in the presence of hydrogen chloride and methanol. Moreover, the reaction (3) is a reaction for adding a substituent to an amino group, which can be performed in the presence of a base and an alkyl halide or an acyl halide. In addition, the reaction (3) can also be performed by condensation in the presence of a carboxylic acid.

2. Pin1 Inhibitors

Pin1 refers to a kind of peptidyl-prolyl cis-trans isomerase (PPIase) that catalyzes cis/trans isomerization of proline residues in proteins, and is an enzyme that specifically acts on proline residues immediately preceded by phosphorylated serine or threonine to change the conformation of those proline residues.

A Pin1 inhibitor according to the present invention is a compound that inhibits the function of Pin1, and a compound represented by the Formula (I) described in the above section 1-1, or a salt thereof, can be used as the Pin1 inhibitor.

In the present invention, the phrase "inhibit the function of Pin1" means inhibiting the isomerase activity of Pin1 and/or the activity of Pin1 to associate or interact with another protein, such as IRS-1.

The activity of a Pin1 inhibitor according to the present invention to inhibit the function of Pin1 can be measured by, for example, but not limited to, examining AMPK (AMP-activated protein kinase) phosphorylation level as an index (see Yusuke Nakatsu et al., Journal of Biological Chemistry, 2015, Vol. 290, No. 40, pp. 24255-24266). Alternatively, the activity of a Pin1 inhibitor according to the present invention to inhibit the function of Pin1 can also be measured by detecting a change in the isomerase activity of Pin1 against a peptide substrate as a change in absorbance (see Hailong Zhao et al., Bioorganic & Medicinal Chemistry, 2016, Vol. 24, pp. 5911-5920). Alternatively, the activity of a Pin1 inhibitor according to the present invention to inhibit the function of Pin1 can also be measured by detecting the association of the inhibitor with Pin1, which competes with the association of Pin1 with a peptide substrate (see Shuo Wei et al., Nature Medicine, Vol. 21, No. 5, pp. 457-466, online methods).

3. Pharmaceutical Compositions

A pharmaceutical composition according to the present invention is a composition comprising a compound represented by the Formula (I) or a pharmaceutically acceptable salt thereof and a pharmaceutically acceptable carrier.

The structure of the compound represented by the Formula (I) is as described in the above section 1-1.

Pharmaceutical compositions according to the present invention can treat or prevent various diseases based on inhibition of Pin1 function as a mechanism of action.

In cases where the compound represented by the Formula (I) has an acidic functional group in the molecule, examples of a pharmaceutically acceptable salt of the compound can include, but are not limited to, sodium, potassium, and ammonium salts. Additionally, in cases where the compound has a basic functional group in the molecule, examples of a pharmaceutically acceptable salt of the compound can include, but are not limited to, hydrochloride, phosphate, acetate, phthalate, fumarate, and oxalate salts.

A pharmaceutical composition according to the present invention can be prepared by combining a compound represented by the Formula (I) or a pharmaceutically acceptable salt thereof and a pharmaceutically acceptable carrier, and may be made in the form of, for example, but not limited to, tablets, granules, capsules, powders, liquids, injection solutions, suppositories, patches, eye drops, and inhalants.

As a pharmaceutically acceptable carrier used in a pharmaceutical composition according to the present invention, various inorganic or organic carrier materials can be used. When the pharmaceutical composition is prepared in solid formulation, such as a tablet or a granule, an excipient, a lubricant, a binder, a disintegrator, and the like can be used. When the pharmaceutical composition is prepared in liquid formulation, such as a liquid or an injection solution, a solvent, a solubilizing agent, a suspending agent, a buffering agent, and the like can be used.

Moreover, additives such as antioxidant, antiseptic agent, and coloring agent can also be used as necessary.

Non-limiting examples of an excipient that can be used include lactose, D-mannitol, and starch; non-limiting examples of a lubricant that can be used include magnesium stearate and talc; non-limiting examples of a binder that can be used include crystalline cellulose and gelatin; non-limiting examples of a disintegrator that can be used include carboxymethyl cellulose.

Moreover, examples of a solvent that can be used include distilled water, alcohols, and propylene glycol; examples of a solubilizing agent that can be used include polyethylene glycol and ethanol; examples of a suspending agent that can be used include stearyl triethanolamine and sodium lauryl sulfate; examples of a buffering agent that can be used include phosphate and acetate salts.

4. Therapeutic or Prophylactic Agents for Inflammatory Disease with Fibrosis

Therapeutic or prophylactic agents for inflammatory diseases associated with fibrosis according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 3.

In the present invention, inflammatory diseases associated with fibrosis refer to diseases that lead to fibrosis due to chronic tissue inflammation, including non-alcoholic steatohepatitis, inflammatory bowel disease, and pulmonary fibrosis.

In the present invention, "non-alcoholic steatohepatitis," which is also called NASH (Non-Alcoholic SteatoHepatitis), refers to a severe type of non-alcoholic fatty liver disease characterized by an accumulation of fat in the liver, which is similar to that found in cases of alcoholic hepatitis and is observed even in a patient who has no history of alcohol intake sufficient to induce liver injury. Non-alcoholic steatohepatitis is known to cause liver cirrhosis, in which dead liver cells are replaced by fibrous tissue.

In the present invention, "inflammatory bowel disease" is a collective term for diseases that cause chronic inflammation and/or ulcers in the mucosa of the large and small intestinal tracts. Ulcerative colitis and Crohn's disease are included as representative examples of inflammatory bowel disease. Ulcerative colitis is a disease that causes chronic inflammation and ulcers in the large intestine, while Crohn's disease is a disease that causes inflammatory lesions, such as ulcer and swelling, in any part of the digestive tract. In cases of stenosis due to intestinal fibrosis caused by inflammatory bowel disease, surgery should be performed.

In the present invention, "pulmonary fibrosis" is a disease that causes chronic inflammation in lung tissue, which is followed by hardening of the inflamed lung tissue due to fibrosis, and eventually impairs lung expansion and contraction.

The therapeutic or prophylactic agents for inflammatory diseases associated with fibrosis according to the present invention contain a compound represented by the Formula (I) or a pharmaceutically acceptable salt thereof as an active ingredient and thereby have an alleviating effect on the conditions of inflammatory diseases associated with fibrosis, such as non-alcoholic steatohepatitis (NASH), inflammatory bowel disease, and pulmonary fibrosis, or a prophylactic effect on the development of inflammatory diseases associated with fibrosis. Such beneficial effects are considered to be based on inhibition of Pin1 function as the mechanism of action of the compound represented by the Formula (I) or the pharmaceutically acceptable salt thereof.

In the therapeutic or prophylactic agents for inflammatory diseases associated with fibrosis according to the present invention, the compound represented by the Formula (I) and contained as an active ingredient is highly variable in terms of chemical structure, due to, for example, $R_1$, $R_2$, and $R_3$. Thus, the chemical structures of the therapeutic or prophylactic agents for inflammatory diseases associated with fibrosis according to the present invention can be modified to obtain, for example, suitable absorption, distribution, degradation, and excretion features.

The therapeutic or prophylactic agents for inflammatory diseases associated with fibrosis according to the present invention can be administered as therapeutic or prophylactic agents for inflammatory diseases associated with fibrosis, such as non-alcoholic steatohepatitis, inflammatory bowel disease, and pulmonary fibrosis, not only to patients diagnosed with these diseases but also to patients suspected of having or at risk of these diseases.

The therapeutic or prophylactic agents for inflammatory diseases associated with fibrosis according to the present invention may be formulated in various dosage forms, which are combined with pharmaceutically acceptable carriers, as described in the above section 3.

When used as a therapeutic or prophylactic agent for non-alcoholic steatohepatitis, the therapeutic or prophylactic agent can be made in the form of, for example, but not limited to, tablets, granules, capsules, powders, and liquids for oral administration, and can also be administered in the form of injection solution directly to the liver by, for example, tube feeding, from the viewpoint of allowing the therapeutic or prophylactic agent to act directly on the liver and thereby to reduce side effects.

When used as a therapeutic or prophylactic agent for inflammatory bowel disease, the therapeutic or prophylactic agent is preferably made in the form of, but not limited to, tablets, granules, capsules, powders, liquids, or suppositories, from the viewpoint of allowing the therapeutic or prophylactic agent to act directly on the intestine.

When used as a therapeutic or prophylactic agent for pulmonary fibrosis, the therapeutic or prophylactic agent is preferably made in the form of, for example, but not limited to, inhalants, from the viewpoint of allowing the therapeutic or prophylactic agent to act directly on the lung.

The therapeutic or prophylactic agents for inflammatory diseases associated with fibrosis according to the present invention should preferably be administered to a patient at a daily dose of 0.01 to 100 mg, more preferably 0.1 to 10 mg, of active ingredient per kg of body weight.

The therapeutic or prophylactic agents for inflammatory diseases associated with fibrosis according to the present invention may contain a compound according to the present invention or a pharmaceutically acceptable salt thereof and further contain active ingredients in at least one or more drugs selected from the group of therapeutic or prophylactic agents for the inflammatory diseases associated with fibrosis.

Examples of the active ingredients that can be used include, but are not limited to, adrenocorticosteroid, anti-TNFα antibodies, 5-ASA (5-aminosalicylic acid; Mesalazine), and obeticholic acid (6-ethyl-chenodeoxycholic acid).

Additionally, the therapeutic or prophylactic agents for inflammatory diseases associated with fibrosis according to the present invention may be used in combination with other therapeutic or prophylactic agents for the inflammatory diseases associated with fibrosis.

5. Therapeutic or Prophylactic Agents for Cancer

Therapeutic or prophylactic agents for cancer according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 3.

The therapeutic or prophylactic agents for cancer according to the present invention have an effect to inhibit cancer growth or an effect to prevent cancer development. Such beneficial effects are considered to be based on inhibition of Pin1 function as the mechanism of action of the compound represented by the Formula (I) or the pharmaceutically acceptable salt thereof.

The therapeutic or prophylactic agents for cancer according to the present invention can be used against cancer, such as colon cancer, prostate cancer, brain tumors, larynx cancer, lung cancer, breast cancer, esophagus cancer, gastric cancer, duodenal cancer, liver cancer, gallbladder cancer, bile duct cancer, pancreatic cancer, kidney cancer, ovarian cancer, cervical cancer, bladder cancer, testicular cancer, leukemia, lymphoma, and multiple myeloma.

The therapeutic or prophylactic agents for cancer according to the present invention can be suitably used as therapeutic or prophylactic agents for colon cancer or prostate cancer.

In the therapeutic or prophylactic agents for cancer according to the present invention, the compound represented by the Formula (I) and contained as an active ingredient is highly variable in terms of chemical structure, due to, for example, $R_1$, $R_2$, and $R_3$. Thus, the chemical structures of the therapeutic or prophylactic agents for cancer according to the present invention can be modified to obtain, for example, suitable absorption, distribution, degradation, and excretion features.

The therapeutic or prophylactic agents for cancer according to the present invention can be administered as therapeutic or prophylactic agents for cancer not only to patients diagnosed with cancer but also to patients suspected of having or at risk of cancer.

Particularly, the prophylactic agents according to the present invention are effectively administered to patients at risk of colon cancer. In this respect, examples of the patients at risk of colon cancer include, but are not limited to, patients with familial polyposis *coli*, Lynch syndrome, MUTYH-associated polyposis *coli*, Peutz-Jeghers syndrome, juvenile polyposis, Cowden disease, Crohn's disease, ulcerative colitis, Cronkhite-Canada syndrome, and the like.

The therapeutic or prophylactic agents for cancer according to the present invention may be formulated in various dosage forms, which are combined with pharmaceutically acceptable carriers, as described in the above section 3.

The therapeutic or prophylactic agents for cancer according to the present invention should preferably be administered to a patient at a daily dose of 0.01 to 100 mg, more preferably 0.1 to 10 mg, of active ingredient per kg of body weight.

The therapeutic or prophylactic agents for cancer according to the present invention may contain a compound according to the present invention or a pharmaceutically acceptable salt thereof and further contain active ingredients in at least one or more drugs selected from the group of therapeutic or prophylactic agents for cancer.

Examples of the active ingredients that can be used include, but are not limited to, oxaliplatin, cisplatin, cyclophosphamide, fluorouracil, irinotecan, doxorubicin, bevacizumab, and cetuximab.

Additionally, the therapeutic or prophylactic agents for cancer according to the present invention can be used in combination with other therapeutic or prophylactic agents for cancer.

6. Therapeutic or Prophylactic Agents for Obesity

Therapeutic or prophylactic agents for obesity according to the present invention contain a compound represented by the Formula (I) or a pharmaceutically acceptable salt thereof as an active ingredient.

The structure of the compound represented by the Formula (I) is as described in the above section 1-1, while the pharmaceutically acceptable salt thereof is as described in the above section 3.

The therapeutic or prophylactic agents for obesity according to the present invention have an effect to reduce accumulation of body fat and thereby to treat or prevent obesity. Such beneficial effects are considered to be based on inhibition of Pin1 function as the mechanism of action of the compound represented by the Formula (I) or the pharmaceutically acceptable salt thereof.

In the therapeutic or prophylactic agents for obesity according to the present invention, the compound represented by the Formula (I) and contained as an active ingredient is highly variable in terms of chemical structure, due to, for example, $R_1$, $R_2$, and $R_3$. Thus, the chemical structures of the therapeutic or prophylactic agents for obesity according to the present invention can be modified to obtain, for example, suitable absorption, distribution, degradation, and excretion features.

In the present invention, "obesity" refers to a condition with excessive fat accumulation in the internal organs or under the skin, which can be diagnosed with, for example, abdominal fat area measured by abdominal CT scanning. The therapeutic or prophylactic agents for obesity according to the present invention can be administered as therapeutic or prophylactic agents for obesity not only to patient diagnosed with obesity but also to patients suspected of having or at risk of obesity.

The therapeutic or prophylactic agents for obesity according to the present invention may be formulated in various dosage forms, which are combined with pharmaceutically acceptable carriers, as described in the above section 3.

The therapeutic or prophylactic agents for obesity according to the present invention should preferably be administered to a patient at a daily dose of 0.01 to 100 mg, more preferably 0.1 to 10 mg, of active ingredient per kg of body weight.

The therapeutic or prophylactic agents for obesity according to the present invention may contain a compound according to the present invention or a pharmaceutically acceptable salt thereof and further contain active ingredients in at least one or more drugs selected from the group of therapeutic or prophylactic agents for obesity.

Examples of the active ingredients that can be used include, but are not limited to, cetilistat, orlistat, and lorcaserin.

Additionally, the therapeutic or prophylactic agents for obesity according to the present invention can be used in combination with other therapeutic or prophylactic agents for obesity.

Now, the present invention will be described in detail by reference to examples, but the present invention is not limited thereto.

EXAMPLES

Example 1

Synthesis of Compounds (Example 1-1) Synthesis of Intermediates

Intermediates (H-122 and H-64) used for the synthesis of compounds according to the present invention were produced.

A known compound represented by the following structural formula (H-122) was synthesized from anthranilic acid as a starting material by two steps according to a method described in J. Org. Chem., 2001, vol. 66, pp. 2784-2788.

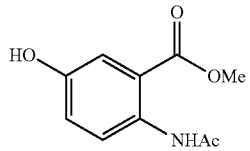

H-122

A known compound represented by the following structural formula (H-64) was synthesized from anthranilic acid as a starting material by four steps according to a method described in J. Org. Chem., 2001, vol. 66, pp. 2784-2788.

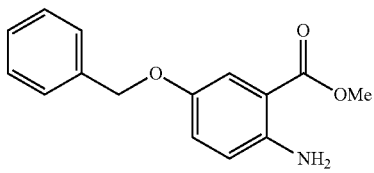

H-64

(Example 1-2) Synthesis of H-68

To a solution of H-64 (400 mg, 1.56 mmol) and 2-naphthoyl chloride (327 mg, 1.72 mmol) in dichloromethane (5 mL), triethylamine (316 mg, 0.44 mL, 3.12 mmol) was added at room temperature, and the resulting mixture was stirred at the same temperature for 13 hours. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (chloroform:ethyl acetate, 15:1) to give H-68 as a white crystal (531 mg, 1.29 mmol, 83%).

The measured NMR spectrum and HR-ESI-MS result of H-68 are described below.

$^1$H NMR (400 MHz, CDCl$_3$) δ 3.99 (3H, s), 5.11 (2H, s), 7.28 (1H, dd, J=9.2, 3.2 Hz), 7.32-7.48 (5H, m), 7.54-7.62 (2H, m), 7.70 (1H, d, J=3.2 Hz), 7.88-7.93 (1H, m), 7.97 (1H, d, J=8.8 Hz), 8.01-8.05 (1H, m), 8.09 (1H, dd, J=8.7, 1.8 Hz), 8.57 (1H, bs), 8.92 (1H, d, J=9.2 Hz), 12.0 (1H, bs); HRESIMS calcd for C$_{26}$H$_{22}$NO$_4$ [M+H]$^+$ 412.1549, found 412.1550.

The identified chemical structure of H-68 is indicated below.

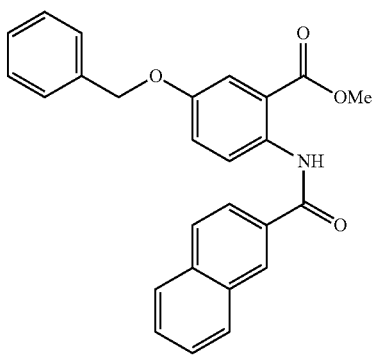 [SMILES: COC(=O)c1cc(OCc2ccccc2)ccc1NC(=O)c1ccc2ccccc2c1]

H-68

(Example 1-3) Synthesis of H-77

To a solution of H-68 (300 mg, 0.73 mmol) in THF (8 mL), an aqueous lithium hydroxide solution (1 M, 2.2 mL, 2.2 mmol) was added at room temperature, and the resulting mixture was stirred at the same temperature for 4 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-77 as a white crystal (280 mg, 0.705 mmol, 97%).

The measured NMR spectrum and HR-ESI-MS result of H-77 are described below.

$^1$H NMR (400 MHz, DMSOd$_6$) δ 5.16 (2H, s), 7.31-7.43 (4H, m), 7.45-7.49 (2H, m), 7.60-7.69 (3H, m), 7.99 (1H, dd, J=8.7, 1.8 Hz), 8.00-8.05 (1H, m), 8.06-8.12 (2H, m), 8.55 (1H, bs), 8.61 (1H, d, J=9.1 Hz), 12.0 (1H, bs); HRESIMS calcd for C$_{25}$H$_{19}$NO$_4$Na [M+Na]$^+$ 420.1212, found 420.1218.

The identified chemical structure of H-77 is indicated below.

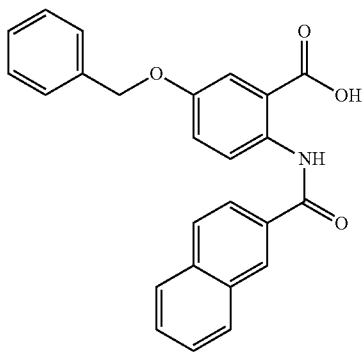 [SMILES: O=C(Nc1ccc(OCc2ccccc2)cc1C(=O)O)c1ccc2ccccc2c1]

H-77

(Example 1-4) Synthesis of H-182

To a solution of H-122 (2.0 g, 9.57 mmol) in acetone (50 mL), potassium carbonate (4.0 g, 28.7 mmol) and 2-bromomethylnaphthalene (3.2 g, 14.4 mmol) were added at room temperature, and the resulting mixture was refluxed for 3 hours. The mixture was cooled down to room temperature and then filtered, and the filtrate was concentrated under reduced pressure. Hexane was added to the residue to dissolve soluble substances. The resulting suspension was filtered, and the remaining solid was washed with hexane to give H-182 as a white crystal (3.05 g, 8.74 mmol, 91%).

The measured NMR spectrum and HR-ESI-MS result of H-182 are described below.

$^1$H NMR (400 MHz, DMSOd$_6$) δ2.05 (3H, s), 3.82 (3H, s), 5.28 (2H, s), 7.31 (1H, dd, J=8.7, 2.7 Hz), 7.46-7.55 (3H, m), 7.57 (1H, d, J=8.6 Hz), 7.88-8.01 (5H, m), 10.19 (1H, s); HRESIMS calcd for C$_{21}$H$_{19}$NO$_4$Na [M+Na]$^+$ 372.1212, found 372.1212.

The identified chemical structure of H-182 is indicated below.

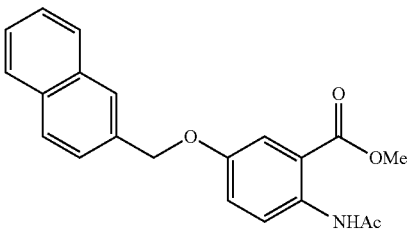 [SMILES: COC(=O)c1cc(OCc2ccc3ccccc3c2)ccc1NC(C)=O]

H-182

(Example 1-5) Synthesis of H-297

To a solution of H-182 (200 mg, 0.573 mmol) in THF (5 mL), an aqueous lithium hydroxide solution (1 M, 1.5 mL, 1.5 mmol) was added at room temperature, and the resulting mixture was stirred at the same temperature for 3 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-297 as a white powder (189 mg, 0.564 mmol, 99%).

The measured NMR spectrum and HR-ESI-MS result of H-297 are described below.

$^1$H NMR (400 MHz, DMSOd$_6$) δ 2.05 (3H, s), 5.26 (2H, s), 7.22 (1H, dd, J=9.1, 3.2 Hz), 7.47-7.60 (4H, m), 7.87-7.99 (4H, m), 8.31 (1H, d, J=8.7 Hz); HRESIMS calcd for C$_{20}$H$_{18}$NO$_4$ [M+H]$^+$ 336.1236, found 336.1249.

The identified chemical structure of H-297 is indicated below.

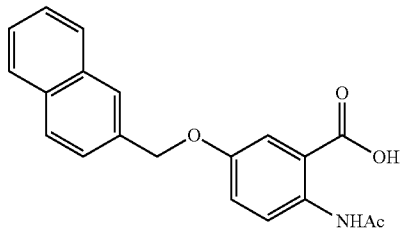 [SMILES: CC(=O)Nc1ccc(OCc2ccc3ccccc3c2)cc1C(=O)O]

H-297

(Example 1-6) Synthesis of H-300

Acetyl chloride (3 mL) was dropped into methanol (36 mL), and the resulting mixture was stirred at room temperature for 1 hour. H-182 (790 mg, 2.26 mmol) was added to the mixed solution, and the resulting mixture was refluxed for 4 hours. The mixture was cooled down to room temperature and then concentrated. Water (45 mL) was added to the residue, and the resulting mixture was adjusted to pH 10 with 2 M aqueous sodium hydroxide solution and then extracted with ether. The organic layer was washed with water and saturated brine, dried over anhydrous magnesium sulfate, and then filtered and concentrated under reduced pressure to give H-300 as a brown crystal (659 mg, 2.15 mmol, 95%).

The measured NMR spectrum and HR-ESI-MS result of H-300 are described below.

$^1$H NMR (400 MHz, DMSOd$_6$) δ 3.77 (3H, s), 5.14 (2H, s), 6.33 (2H, bs), 6.76 (1H, d, J=9.1 Hz), 7.10 (1H, dd, J=9.2, 2.7 Hz), 7.34 (1H, d, J=3.1 Hz), 7.44-7.57 (3H, m), 7.86-7.96 (4H, m); HRESIMS calcd for C$_{19}$H$_{18}$NO$_3$ [M+H]$^+$ 308.1287, found 308.1284.

The identified chemical structure of H-300 is indicated below.

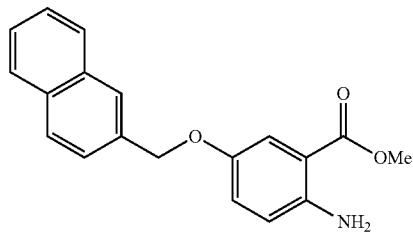 [SMILES: COC(=O)c1cc(OCc2ccc3ccccc3c2)ccc1N]

H-300

(Example 1-7) Synthesis of H-443

To a solution of H-300 (200 mg, 0.65 mmol) in THF (4 mL), an aqueous lithium hydroxide solution (1 M, 2.0 mL, 2.0 mmol) was added at room temperature, and the resulting mixture was stirred at the same temperature for 13 hours. The mixture was neutralized by adding 1 M hydrochloric acid (2.0 mL, 2.0 mmol) thereto, and the separated solid was collected by suction filtration and washed with water to give H-443 as a white powder (122 mg, 0.42 mmol, 65%).

The measured NMR spectrum and HR-ESI-MS result of H-443 are described below.

$^1$H NMR (400 MHz, DMSOd$_6$) δ 5.14 (2H, s), 6.70 (1H, d, J=9.2 Hz), 7.05 (1H, dd, J=9.1, 3.2 Hz), 7.32 (1H, d, J=3.2 Hz), 7.47-7.54 (2H, m), 7.55 (1H, dd, J=8.3, 1.4 Hz), 7.88-7.95 (4H, m); HRESIMS calcd for C$_{18}$H$_{16}$NO$_3$ [M+H]$^+$ 294.1130, found 294.1130.

The identified chemical structure of H-443 is indicated below.

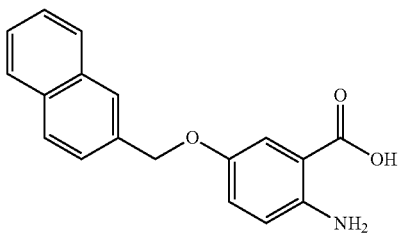 [SMILES: Nc1ccc(OCc2ccc3ccccc3c2)cc1C(=O)O]

H-443

(Example 1-8) Synthesis of H-305

To a solution of H-64 (200 mg, 0.78 mmol) and 2-naphthalenesulfonyl chloride (212 mg, 0.934 mmol) in dichloromethane (4 mL), triethylamine (95 mg, 0.13 mL, 0.934 mmol) was added at room temperature, and the resulting mixture was stirred at the same temperature for 16 hours. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (hexane:ethyl acetate, 3:1) to give H-305 as a white crystal (332 mg, 0.74 mmol, 96%).

The measured NMR spectrum and HR-ESI-MS result of H-305 are described below.

$^1$H NMR (400 MHz, CDCl$_3$) δ 3.73 (3H, s), 4.97 (2H, s), 7.11 (1H, dd, J=9.2, 3.2 Hz), 7.29-7.45 (6H, m), 7.54-7.65 (2H, m), 7.70-7.75 (2H, m), 7.82-7.92 (3H, m), 8.35 (1H, bs), 10.17 (1H, bs); HRESIMS calcd for C$_{25}$H$_{21}$NO$_5$SNa [M+Na]$^+$ 470.1038, found 470.1036.

The identified chemical structure of H-305 is indicated below.

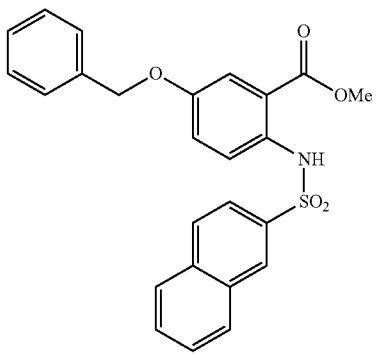 [SMILES: COC(=O)c1cc(OCc2ccccc2)ccc1NS(=O)(=O)c1ccc2ccccc2c1]

H-305

(Example 1-9) Synthesis of H-338

To a solution of H-305 (255 mg, 0.57 mmol) in THF (5 mL), an aqueous lithium hydroxide solution (1 M, 1.5 mL, 1.5 mmol) was added at room temperature, and the resulting mixture was stirred at the same temperature for 13 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-338 as a white powder (200 mg, 0.46 mmol, 81%).

The measured NMR spectrum and HR-ESI-MS result of H-338 are described below.

$^1$H NMR (400 MHz, DMSOd$_6$) δ 5.01 (2H, s), 7.19-7.44 (7H, m), 7.50 (1H, d, J=7.6 Hz), 7.60-7.74 (3H, m), 7.94-8.15 (3H, m), 8.46 (1H, bs), 10.75 (1H, bs); HRESIMS calcd for C$_{24}$H$_{29}$NO$_5$SNa [M+Na]$^+$ 456.0882, found 456.0878.

The identified chemical structure of H-338 is indicated below.

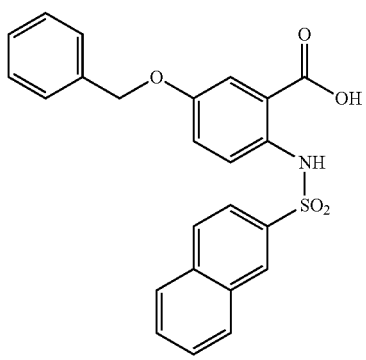 [SMILES: O=C(O)c1cc(OCc2ccccc2)ccc1NS(=O)(=O)c1ccc2ccccc2c1]

H-338

(Example 1-10) Synthesis of H-306

To a solution of H-64 (200 mg, 0.78 mmol) and 2-quinaldic acid (162 mg, 0.934 mmol) in dichloromethane (4 mL), DMAP (9.5 mg, 0.078 mmol) and EDCI (194 mg, 1.01 mmol) were added at room temperature, and the resulting mixture was stirred at the same temperature for 16 hours. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (hexane:ethyl acetate, 3:1) to give H-306 as a white crystal (288 mg, 0.70 mmol, 90%).

The measured NMR spectrum and HR-ESI-MS result of H-306 are described below.

$^1$H NMR (400 MHz, CDCl$_3$) δ 4.06 (3H, s), 5.11 (2H, s), 7.27 (1H, dd, J=9.2, 3.2 Hz), 7.32-7.49 (5H, m), 7.64 (1H, ddd, J=8.2, 6.9, 1.4 Hz), 7.73 (1H, d, J=3.2 Hz), 7.81 (1H, ddd, J=8.2, 6.8, 1.3 Hz), 7.90 (1H, d, J=7.8 Hz), 8.30-8.40 (3H, m), 8.95 (1H, d, J=9.2 Hz); HRESIMS calcd for C$_{25}$H$_{21}$N$_2$O$_4$ [M+H]$^+$ 413.1501, found 413.1500.

The identified chemical structure of H-306 is indicated below.

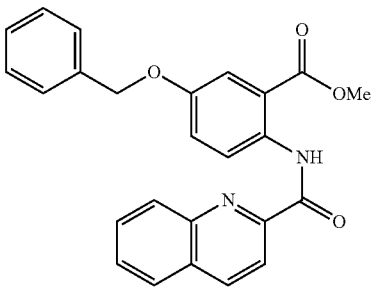 [SMILES: COC(=O)c1cc(OCc2ccccc2)ccc1NS(=O)(=O)c1ccc2ccccc2c1]

H-306

(Example 1-11) Synthesis of H-339

To a solution of H-306 (224 mg, 0.54 mmol) in THF (5 mL), an aqueous lithium hydroxide solution (1 M, 2.2 mL, 2.2 mmol) was added at room temperature, and the resulting mixture was stirred at the same temperature for 13 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure. The obtained residue was washed with ether to give H-339 as a pale yellow powder (134 mg, 0.34 mmol, 62%).

The measured NMR spectrum and HR-ESI-MS result of H-339 are described below.

$^1$H NMR (400 MHz, DMSOd$_6$) δ 5.14 (2H, s), 7.24-7.50 (6H, m), 7.61-7.87 (3H, m), 8.04-8.19 (2H, m), 8.25 (1H, d, J=8.6 Hz), 8.58 (1H, d, J=8.0 Hz), 8.83 (1H, d, J=9.1 Hz); HRESIMS calcd for C$_{24}$H$_{19}$N$_2$O$_4$ [M+H]$^+$ 399.1345, found 399.1339.

The identified chemical structure of H-339 is indicated below.

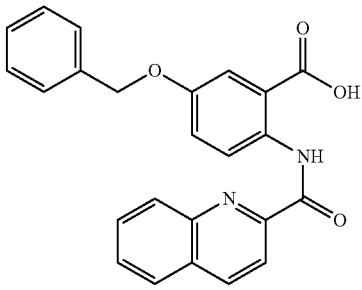 [SMILES: O=C(O)c1cc(OCc2ccccc2)ccc1NS(=O)(=O)c1ccc2ccccc2n1]

H-339

(Example 1-12) Synthesis of H-312

To a solution of H-64 (200 mg, 0.78 mmol) and 2-naphthyloxyacetic acid (189 mg, 0.934 mmol) in dichloromethane (4 mL), DMAP (9.5 mg, 0.078 mmol) and EDCI (194 mg, 1.01 mmol) were added at room temperature, and the resulting mixture was stirred at the same temperature for 16 hours. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (hexane:ethyl acetate, 3:1) to give H-312 as a white powder (340 mg, 0.77 mmol, 99%).

The measured NMR spectrum and HR-ESI-MS result of H-312 are described below.

$^1$H NMR (400 MHz, CDCl$_3$) δ 3.94 (3H, s), 4.76 (2H, s), 5.08 (2H, s), 7.19-7.23 (2H, m), 7.31-7.50 (8H, m), 7.64 (1H, d, J=3.2 Hz), 7.74-7.85 (3H, m), 8.74 (1H, d, J=9.1 Hz), 11.89 (1H, s); HRESIMS calcd for C$_{27}$H$_{24}$NO$_5$ [M+H]$^+$ 442.1654, found 442.1655.

The identified chemical structure of H-312 is indicated below.

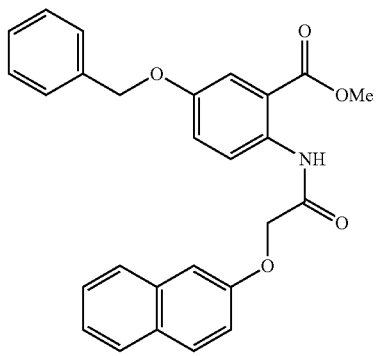 [SMILES: COC(=O)c1cc(OCc2ccccc2)ccc1NC(=O)COc1ccc2ccccc2c1]

H-312

(Example 1-13) Synthesis of H-362

To a solution of H-312 (252 mg, 0.57 mmol) in THF (5 mL), an aqueous lithium hydroxide solution (1 M, 2.0 mL, 2.0 mmol) was added at room temperature, and the resulting mixture was stirred at the same temperature for 13 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-362 as a white powder (243 mg, 0.57 mmol, 100%).

The measured NMR spectrum and HR-ESI-MS result of H-362 are described below.

$^1$H NMR (400 MHz, DMSOd$_6$) δ 4.75 (2H, s), 5.07 (2H, s), 7.11 (1H, dd, J=8.7, 2.7 Hz), 7.27-7.48 (9H, m), 7.71 (1H, d, J=2.8 Hz), 7.77-7.86 (3H, m), 8.58 (1H, d, J=9.1 Hz); HRESIMS calcd for C$_{26}$H$_{21}$NO$_5$Na [M+Na]$^+$ 450.1317, found 450.1320.

The identified chemical structure of H-362 is indicated below.

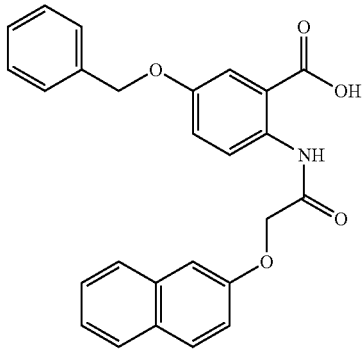 [SMILES: O=C(COc1ccc2ccccc2c1)Nc1ccc(OCc2ccccc2)cc1C(=O)O]

H-362

(Example 1-14) Synthesis of H-313

To a solution of H-64 (200 mg, 0.78 mmol) and 3-phenoxy benzoic acid (200 mg, 0.934 mmol) in dichloromethane (4 mL), DMAP (9.5 mg, 0.078 mmol) and EDCI (194 mg, 1.01 mmol) were added at room temperature, and the resulting mixture was stirred at the same temperature for 16 hours. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (hexane:ethyl acetate, 3:1) to give H-313 as a pale yellow powder (284 mg, 0.627 mmol, 81%).

The measured NMR spectrum and HR-ESI-MS result of H-313 are described below.

$^1$H NMR (400 MHz, CDCl$_3$) δ 3.94 (3H, s), 5.09 (2H, s), 7.08 (2H, d, J=7.3 Hz), 7.15 (1H, t, J=7.3 Hz), 7.19 (1H, dd, J=8.2, 2.3 Hz), 7.24 (1H, dd, J=9.1, 2.7 Hz), 7.31-7.50 (8H, m), 7.65-7.69 (2H, m), 7.72 (1H, d, J=8.2 Hz), 8.83 (1H, d, J=9.2 Hz), 11.77 (1H, s); HRESIMS calcd for C$_{28}$H$_{23}$NO$_5$Na [M+Na]$^+$ 476.1474, found 476.1476.

The identified chemical structure of H-313 is indicated below.

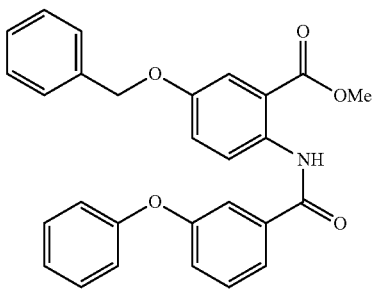 [SMILES: COC(=O)c1cc(OCc2ccccc2)ccc1NC(=O)c1cccc(Oc2ccccc2)c1]

H-313

(Example 1-15) Synthesis of H-363

To a solution of H-313 (228 mg, 0.57 mmol) in THF (5 mL), an aqueous lithium hydroxide solution (1 M, 2.0 mL, 2.0 mmol) was added at room temperature, and the resulting mixture was stirred at the same temperature for 13 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-363 as a brown crystal (219 mg, 0.50 mmol, 100%).

The measured NMR spectrum and HR-ESI-MS result of H-363 are described below.

$^1$H NMR (400 MHz, DMSOd$_6$) δ 5.09 (2H, s), 7.06 (2H, d, J=8.3 Hz), 7.12-7.23 (3H, m), 7.26-7.47 (7H, m), 7.50-7.57 (2H, m), 7.68 (1H, d, J=2.7 Hz), 7.74 (1H, d, J=7.8 Hz), 8.56 (1H, d, J=9.1 Hz); HRESIMS calcd for $C_{27}H_{22}NO_5$ [M+H]$^+$ 440.1498, found 440.1505.

The identified chemical structure of H-363 is indicated below.

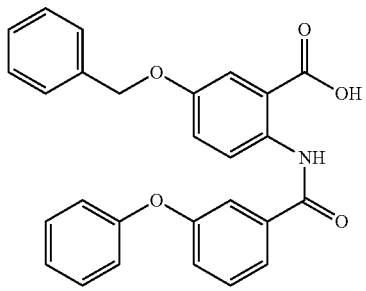 [SMILES: O=C(Nc1ccc(OCc2ccccc2)cc1C(=O)O)c1cccc(Oc2ccccc2)c1]

H-363

(Example 1-16) Synthesis of H-345

To a solution of H-64 (200 mg, 0.78 mmol) and 1-naphthoic acid (161 mg, 0.934 mmol) in dichloromethane (4 mL), DMAP (9.5 mg, 0.078 mmol) and EDCI (194 mg, 1.01 mmol) were added at room temperature, and the resulting mixture was stirred at the same temperature for 16 hours. Water was added to the mixture, and the resulting mixture was extracted with chloroform. The organic layer was washed with saturated brine, dried over anhydrous magnesium sulfate, and then filtered and concentrated under reduced pressure. The residue was purified by silica gel column chromatography (hexane:ethyl acetate, 3:1) to give H-345 as a colorless crystal (288 mg, 0.70 mmol, 90%).

The measured NMR spectrum and HR-ESI-MS result of H-345 are described below.

$^1$H NMR (400 MHz, CDCl$_3$) δ 3.88 (3H, s), 5.11 (2H, s), 7.31 (1H, dd, J=9.6, 3.2 Hz), 7.33-7.50 (5H, m), 7.52-7.61 (3H, m), 7.70 (1H, d, J=3.2 Hz), 7.84-7.92 (2H, m), 7.98 (1H, d, J=8.2 Hz), 8.56 (1H, d, J=8.0 Hz), 8.98 (1H, d, J=9.1 Hz), 11.45 (1H, s); HRESIMS calcd for $C_{26}H_{21}NO_4Na$ [M+Na]$^+$ 434.1368, found 434.1361.

The identified chemical structure of H-345 is indicated below.

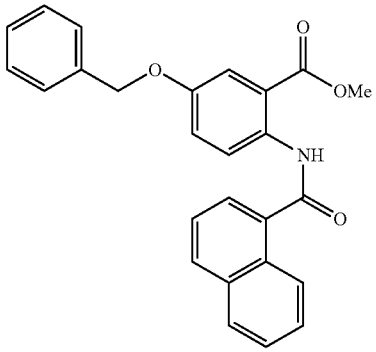 [SMILES: COC(=O)c1cc(OCc2ccccc2)ccc1NC(=O)c1cccc2ccccc12]

H-345

(Example 1-17) Synthesis of H-370

To a solution of H-345 (253 mg, 0.68 mmol) in THF (5 mL), an aqueous lithium hydroxide solution (1 M, 2.8 mL, 2.8 mmol) was added at room temperature, and the resulting mixture was stirred at the same temperature for 13 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-370 as a white powder (234 mg, 0.59 mmol, 87%).

The measured NMR spectrum and HR-ESI-MS result of H-370 are described below. $^1$H NMR (400 MHz, DMSOd$_6$) δ 5.17 (2H, s), 7.30-7.43 (4H, m), 7.45-7.49 (2H, m), 7.57-7.64 (4H, m), 7.86 (1H, dd, J=6.8, 1.4 Hz), 7.99-8.05 (1H, m), 8.10 (1H, d, J=8.2 Hz), 8.33-8.39 (1H, m), 8.55 (1H, d, J=9.1 Hz), 11.43 (1H, s); HRESIMS calcd for $C_{25}H_{19}NO_4Na$ [M+Na]$^+$ 420.1212, found 420.1206.

The identified chemical structure of H-370 is indicated below.

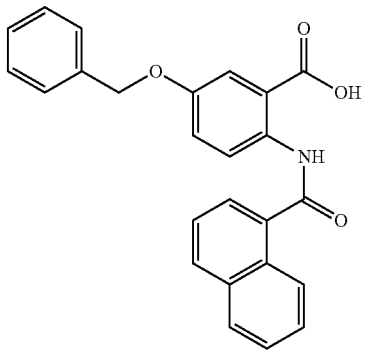 [SMILES: O=C(O)c1cc(OCc2ccccc2)ccc1NC(=O)c1cccc2ccccc12]

H-370

(Example 1-18) Synthesis of H-350

To a solution of H-300 (1.3 g, 4.24 mmol) and 2-naphthoyl chloride (888 mg, 4.66 mmol) in dichloromethane (30 mL), triethylamine (472 mg, 0.65 mL, 4.66 mmol) was added at room temperature, and the resulting mixture was stirred at the same temperature for 13 hours. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:chloroform, 1:3) to give H-350 as a white crystal (1.92 g, 4.17 mmol, 98%).

The measured NMR spectrum and HR-ESI-MS result of H-350 are described below.

$^1$H NMR (400 MHz, CDCl$_3$) δ 3.99 (3H, s), 5.28 (2H, s), 7.34 (1H, dd, J=9.1, 3.2 Hz), 7.47-7.53 (2H, m), 7.54-7.62 (3H, m), 7.75 (1H, d, J=3.2 Hz), 7.83-7.93 (5H, m), 7.97 (1H, d, J=8.7 Hz), 8.03 (1H, d, J=7.3 Hz), 8.09 (1H, dd, J=8.6, 1.8 Hz), 8.57 (1H, s), 8.94 (1H, d, J=9.2 Hz), 11.97 (1H, bs); HRESIMS calcd for C$_{30}$H$_{23}$NO$_4$ [M+H]$^+$ 462.1705, found 462.1703.

The identified chemical structure of H-350 is indicated below.

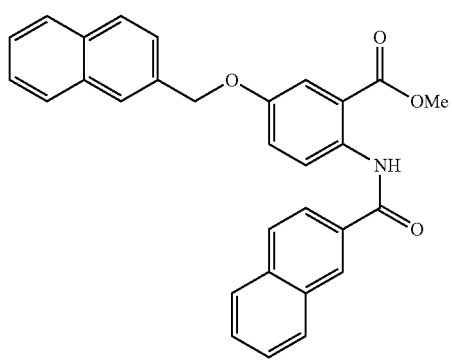 [SMILES: COC(=O)c1cc(OCc2ccc3ccccc3c2)ccc1NC(=O)c1ccc2ccccc2c1]

H-350

(Example 1-19) Synthesis of H-371

To a solution of H-350 (1.0 g, 2.17 mmol) in THF (50 mL), an aqueous lithium hydroxide solution (1 M, 8.7 mL, 8.7 mmol) was added at room temperature, and the resulting mixture was stirred at the same temperature for 13 hours. The mixture was neutralized by adding 1 M hydrochloric acid thereto, and concentrated under reduced pressure to remove THF. The separated solid was filtered by suction, and the remaining solid was washed with water to give H-371 as a white powder (964 mg, 2.16 mmol, 99%).

The measured NMR spectrum and HR-ESI-MS result of H-371 are described below.

$^1$H NMR (400 MHz, DMSOd$_6$) δ 5.34 (2H, s), 7.42 (1H, dd, J=9.2, 3.2 Hz), 7.49-7.56 (2H, m), 7.58-7.69 (4H, m), 7.91-8.05 (6H, m), 8.06-8.12 (2H, m), 8.55 (1H, s), 8.63 (1H, d, J=9.1 Hz); HRESIMS calcd for C$_{29}$H$_{21}$NO$_4$Na [M+Na]$^+$ 470.1368, found 470.1370.

The identified chemical structure of H-371 is indicated below.

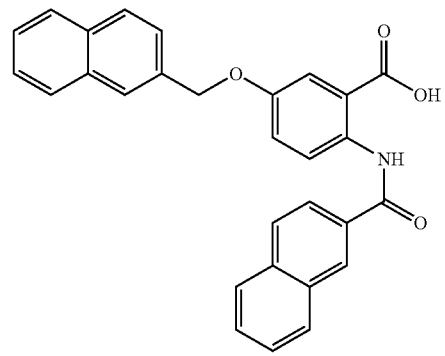 [SMILES: O=C(Nc1ccc(OCc2ccc3ccccc3c2)cc1C(=O)O)c1ccc2ccccc2c1]

H-371

(Example 1-20) Synthesis of H-351

To a solution of H-300 (200 mg, 0.65 mmol) and 2-naphthalenesulfonyl chloride (177 mg, 0.78 mmol) in dichloromethane (4 mL), triethylamine (79 mg, 0.11 mL, 0.78 mmol) was added at room temperature, and the resulting mixture was stirred at the same temperature for 13 hours. Water was added to the mixture, and the resulting mixture was extracted with ethyl acetate. The organic layer was washed with saturated brine, dried over anhydrous magnesium sulfate, and then filtered and concentrated under reduced pressure. The residue was purified by silica gel column chromatography (hexane:ethyl acetate, 2:1) to give H-351 as a brown crystal (289 mg, 0.58 mmol, 89%).

The measured NMR spectrum and HR-ESI-MS result of H-351 are described below.

$^1$H NMR (400 MHz, CDCl$_3$) δ 3.72 (3H, s), 5.14 (2H, s), 7.16 (1H, bd, J=8.7 Hz), 7.43-7.65 (6H, m), 7.68-7.76 (2H, m), 7.78-7.92 (7H, m), 8.35 (1H, s), 10.18 (1H, s); HRESIMS calcd for C$_{29}$H$_{24}$NO$_5$S [M+H]$^+$ 498.1375, found 498.1382.

The identified chemical structure of H-351 is indicated below.

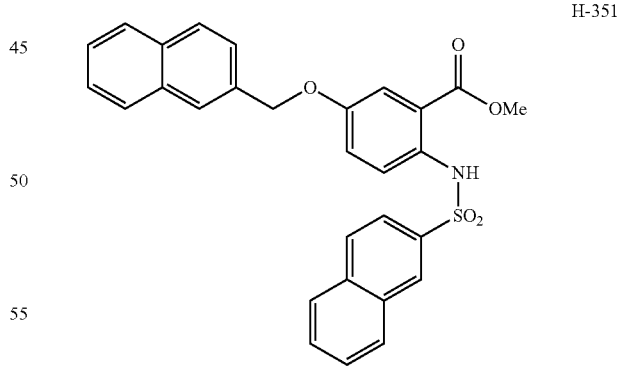

H-351

(Example 1-21) Synthesis of H-376

To a solution of H-351 (190 mg, 0.38 mmol) in THF (3 mL), an aqueous lithium hydroxide solution (1 M, 1.5 mL, 1.5 mmol) was added at room temperature, and the resulting mixture was stirred at the same temperature for 6 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-376 as a brown crystal (178 mg, 0.37 mmol, 97%).

The measured NMR spectrum and HR-ESI-MS result of H-376 are described below.

$^1$H NMR (400 MHz, CDCl$_3$) δ 5.17 (2H, s), 7.21 (1H, dd, J=9.1, 3.2 Hz), 7.43-7.65 (6H, m), 7.69-7.76 (2H, m), 7.79-7.89 (7H, m), 8.38 (1H, s); HRESIMS calcd for C$_{28}$H$_{21}$NO$_5$SNa [M+Na]$^+$ 506.1038, found 506.1041.

The identified chemical structure of H-376 is indicated below.

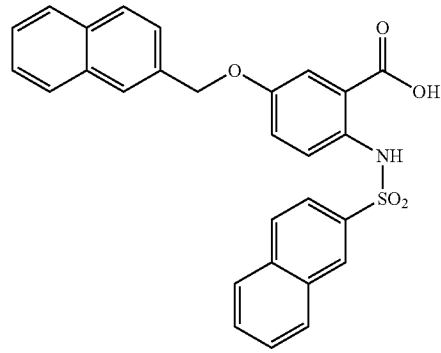 [SMILES: O=C(O)c1cc(OCc2ccc3ccccc3c2)ccc1NS(=O)(=O)c1ccc2ccccc2c1]

H-376

(Comparative Example 1-1) Synthesis of a Compound (H-296) as a Comparative Example A known compound (H-296) was produced as an example for comparison with the compounds according to the present invention.

First, a known compound represented by the following structural formula (H-295) was synthesized as an intermediate from anthranilic acid as a starting material by three steps according to a method described in J. Org. Chem., 2001, vol. 66, pp. 2784-2788.

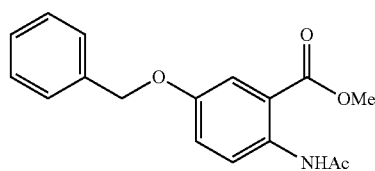

H-295

To a solution of H-295 (200 mg, 0.67 mmol) in THF (5 mL), an aqueous lithium hydroxide solution (1 M, 1.5 mL, 1.5 mmol) was added at room temperature, and the resulting mixture was stirred at the same temperature for 3 hours. The mixture was neutralized by adding 1 M hydrochloric acid thereto, and then extracted with ethyl acetate. The organic layer was washed with saturated brine, dried over anhydrous magnesium sulfate, and then filtered and concentrated under reduced pressure to give H-296 as a white powder (190 mg, 0.67 mmol, 100%).

The measured NMR spectrum and HR-ESI-MS result of H-296 are described below.

$^1$H NMR (400 MHz, DMSOd$_6$) δ 2.03 (3H, s), 5.06 (2H, s), 7.05 (1H, dd, J=9.1, 3.0 Hz), 7.28-7.45 (5H, m), 7.58 (1H, d, J=2.7 Hz), 8.33 (1H, d, J=9.1 Hz), 12.4 (1H, bs); HRESIMS calcd for C$_{16}$H$_{15}$NO$_4$Na [M+Na]$^+$ 308.0899, found 308.0897.

The identified chemical structure of the known compound H-296 is indicated below.

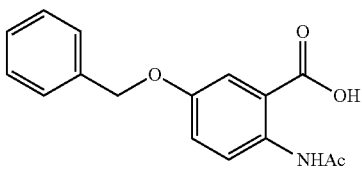 [SMILES: CC(=O)Nc1ccc(OCc2ccccc2)cc1C(=O)O]

H-296

Example 2

(Evaluation of Pin1 Inhibition Activity)

To evaluate the inhibitory activity of each compound synthesized in Example 1 against the function of Pin1, a cell-based assay was performed according to the method previously developed by the inventors (Yusuke Nakatsu et al., Journal of Biological Chemistry, 2015, Vol. 290, No. 40, pp. 24255-24266), in which the phosphorylation level of AMPK (AMP-activated protein kinase), a protein whose phosphorylation is inhibited by Pin1, was examined as an index.

Briefly, 293T cells were plated on a collagen-coated 24-well plate. Forty-eight hours later, each compound synthesized in the preceding example (at 100 μM) was added to the plate, and the plate was left to stand in an incubator for 30 minutes. Subsequently, 10 mM 2-DG was added to the plate, and one hour later, each sample was collected with a buffer containing mercaptoethanol and SDS.

SDS-PAGE and blotting were performed, and blocking was then performed with 3% BSA for 1 hour, according to conventional protocols. Subsequently, a pAMPK antibody (Cell Signaling; diluted 1:2000 in Can Get Signal Solution 1, Toyobo) as a primary antibody, and an HRP-linked anti rabbit IgG (GE Healthcare; diluted 1:4000 in Can Get Signal Solution 2, Toyobo) as a secondary antibody were allowed to react at ambient temperature for 1 hour prior to detection.

The inhibitory activity against the function of Pin1 was evaluated by comparing the inhibition levels between each compound and a known Pin1 inhibitor, C1, as indicated below:

(+++): a higher level of AMPK phosphorylation is promoted, as compared with C1;

(++): a similar level of AMPK phosphorylation is promoted, as compared with C1;

(+): a lower level of AMPK phosphorylation is promoted, as compared with C1;

(−): no or almost no promotion is found in AMPK phosphorylation.

Some of the compounds synthesized in Example 1 were evaluated by the above-described method. The result is as follows:

(+++): H-77 (Example 1-3), H-297 (Example 1-5), H-300 (Example 1-6), (++): H-182 (Example 1-4), (+): H-68 (Example 1-2), H-338 (Example 1-9), H-339 (Example 1-11), H-362 (Example 1-13), H-363 (Example 1-15), H-370 (Example 1-17), H-371 (Example 1-19), H-376 (Example 1-21), H-443 (Example 1-7)

(−): H-296 (Comparative Example 1-1)

The activity was not measured in H-305, H-306, H-312, H-313, H-345, H-350, and H-351, which are esters formed by attachment of a methyl group to the carboxylic acids of H-338, H-339, H-362, H-363, H-370, H-371, and H-376, respectively. These esters can be easily hydrolyzed into carboxylic acids, which are active compounds.

The results are summarized as shown in the following tables.

TABLE 1

| Example No. | Compound No. | Structural formula | Pin1 inhibition activity |
|---|---|---|---|
| Example 1-2 | H-68 | *(structure)* | + |
| Example 1-3 | H-77 | *(structure)* | +++ |
| Example 1-4 | H-182 | *(structure)* | ++ |
| Example 1-5 | H-297 | *(structure)* | +++ |

TABLE 1-continued

| Example No. | Compound No. | Structural formula | Pin1 inhibition activity |
|---|---|---|---|
| Example 1-6 | H-300 | (2-naphthylmethoxy)-substituted methyl 2-amino-benzoate | +++ |

TABLE 2

| Example No. | Compound No. | Structural formula | Pin1 inhibition activity |
|---|---|---|---|
| Example 1-7 | H-443 | (2-naphthylmethoxy)-substituted 2-amino-benzoic acid | + |
| Example 1-8 | H-305 | 5-(benzyloxy)-2-(naphthalene-2-sulfonamido)benzoate methyl ester | Not measured (Hydrolysis causes conversion to H-338, which is active) |
| Example 1-9 | H-338 | 5-(benzyloxy)-2-(naphthalene-2-sulfonamido)benzoic acid | + |

TABLE 2-continued
| Example No. | Compound No. | Structural formula | Pin1 inhibition activity |
|---|---|---|---|
| Example 1-10 | H-306 | 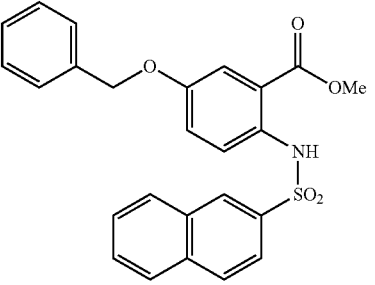 | Not measured (Hydrolysis causes conversion to H-339, which is active) |
| Example 1-11 | H-339 | 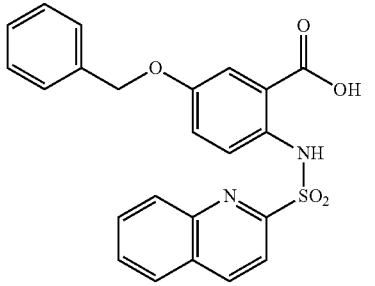 | + |
TABLE 3
| Example No. | Compound No. | Structural formula | Pin1 inhibition activity |
|---|---|---|---|
| Example 1-12 | H-312 | 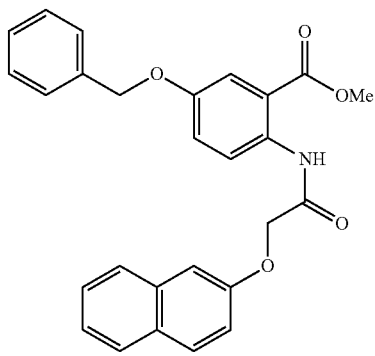 | Not measured (Hydrolysis causes conversion to H-362, which is active) |
| Example 1-13 | H-362 | 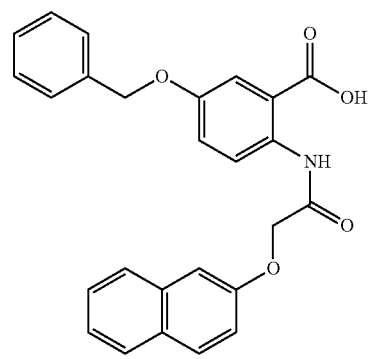 | + |

TABLE 3-continued

| Example No. | Compound No. | Structural formula | Pin1 inhibition activity |
|---|---|---|---|
| Example 1-14 | H-313 | | Not measured (Hydrolysis causes conversion to H-363, which is active) |
| Example 1-15 | H-363 | | + |
| Example 1-16 | H-345 | | Not measured (Hydrolysis causes conversion to H-370, which is active) |

TABLE 4

| Example No. | Compound No. | Structural formula | Pin1 inhibition activity |
|---|---|---|---|
| Example 1-17 | H-370 | | + |

TABLE 4-continued

| Example No. | Compound No. | Structural formula | Pin1 inhibition activity |
|---|---|---|---|
| Example 1-18 | H-350 | | Not measured (Hydrolysis causes conversion to H-371, which is active) |
| Example 1-19 | H-371 | | + |
| Example 1-20 | H-351 | | Not measured (Hydrolysis causes conversion to H-376, which is active) |
| Example 1-21 | H-376 | | + |

TABLE 5

| Example No. | Compound No. | Structural formula | Pin1 inhibition activity |
|---|---|---|---|
| Comparative Example 1-1 | H-296 | benzyl ether of 5-hydroxy-2-acetamidobenzoic acid (phenyl-CH2-O-C6H3(NHAc)-COOH) | — |

Example 3

(NASH Treatment Study)

Example 3-1

Animal experiments were performed using non-alcoholic steatohepatitis (NASH) model mice to test the compounds according to the present invention for the therapeutic effect on NASH.

NASH model mice (hereinafter referred to as "NASH mice") were produced by feeding a high-fat diet containing trans fatty acids (HFDT) to individual male laboratory mice (C57BL/6J) for 8 weeks. The mice were divided into groups, and animal experiments were performed on a group of mice to which a compound according to the present invention (H-77) was administered intraperitoneally at a dose of 2.5 mg/kg/day three times a week, and a group of mice to which Juglone, a known Pin1 inhibitor, was administered intraperitoneally at a dose of 2.5 mg/kg/day three times a week, and a group of mice to which nothing was administered, during the 8-week HFDT feeding period. In addition, a normal diet was given to individual male laboratory mice (C57BL/6J) for 8 weeks to prepare control mice.

The results of measurements of liver weight change and blood AST (GOT) concentration in these mice are shown in FIG. 1 (A) and FIG. 1 (B).

FIG. 1 (A) is a graph depicting the result of measurement of mouse liver weight, and graph bars represent the results of measurement of liver weight in the control mice, the NASH mice given a HFDT, the NASH mice given a HFDT and H-77, and the NASH mice given a HFDT and Juglone, from left to right.

As shown in FIG. 1 (A), the liver weight was increased in the mice given a HFDT as a result of fat accumulation in the liver. In contrast, the increase in liver weight was reduced when H-77 was administered. Additionally, the NASH mice given Juglone were all dead within 8 weeks. Severe side effects were suspected to have occurred because of the low specificity of Juglone as a Pin1 inhibitor.

FIG. 1 (B) is a graph depicting the result of measurement of blood AST (GOT) concentration (IU/ml), and graph bars represent the results of measurement of blood AST in the control mice given a normal diet, the NASH mice given a HFDT, the NASH mice given a HFDT and H-77, and the NASH mice given a HFDT and Juglone, from left to right.

As shown in FIG. 1 (B), the AST value, an index of liver inflammation, was increased in the mice given a HFDT. In contrast, the AST value was decreased and inhibition of liver inflammation was observed when H-77 was administered.

Example 3-2

Figure 2:
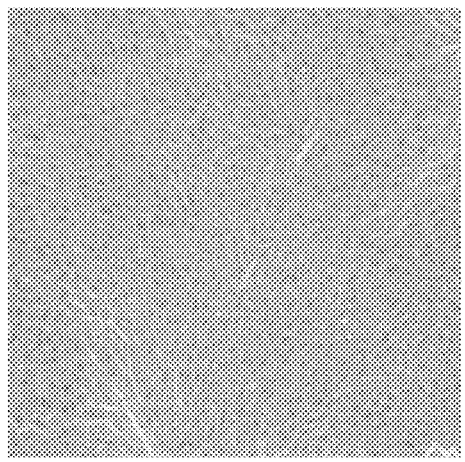
FIG. 2 shows photographs provided instead of drawings and depicting results of microscopic observation of liver tissue sections from mice in a NASH treatment study.
Figure 2:
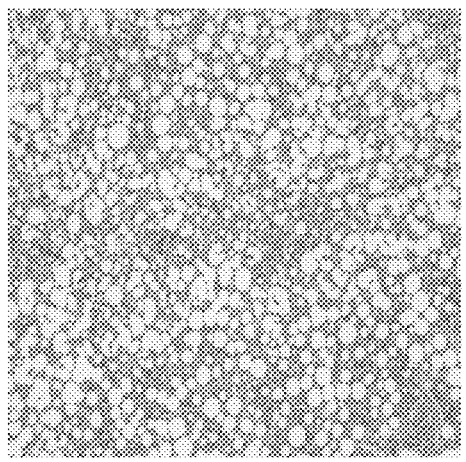
Figure 2:
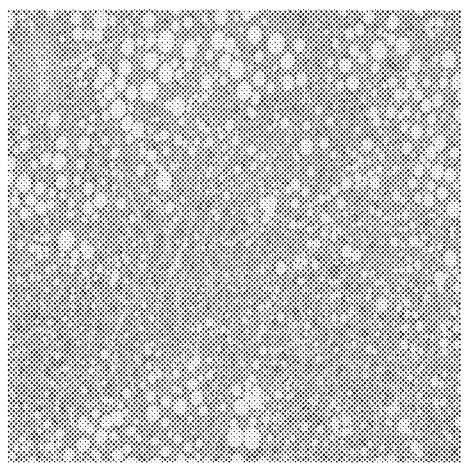

FIG. 2 shows results of microscopic observation of liver tissue sections from the control mice given a normal diet, the NASH mice given a HFDT, and the NASH mice given a HFDT and H-77.

FIG. 2 (A) is a photograph depicting the result of observation of liver tissue from the control mice given a normal diet, and FIG. 2 (B) is a photograph depicting the result of observation of liver tissue from the NASH mice given a HFDT, and FIG. 2 (C) is a photograph depicting the result of observation of liver tissue from the NASH mice given a HFDT and H-77.

No fat accumulation was observed in the liver tissue from the control mice, as shown in FIG. 2 (A), while an accumulation of fat was found in the liver tissue from the NASH mice given a HFDT, as shown in FIGS. 2 (B) and (C). In addition, administration of H-77 reduced fat accumulation even in the NASH mice, as evidenced by the comparison between FIG. 2 (B) and FIG. 2 (C).

Example 3-3

Next, an animal experiment was performed on NASH mice that were produced by feeding a methionine-choline-deficient diet (MCDD).

NASH mice were produced by feeding a methionine-choline-deficient diet (MCDD) to individual male laboratory mice (C57BL/6J) for 8 weeks. The mice were divided into groups, and an animal experiment was performed on a group of mice to which a compound according to the present invention (H-77) was administered intraperitoneally at a dose of 2.5 mg/kg/day three times a week, and a group of mice to which nothing was administered, during the 8-week MCDD feeding period. In addition, a normal diet was given to individual male laboratory mice (C57BL/6J) for 8 weeks to prepare control mice.

Figure 3:
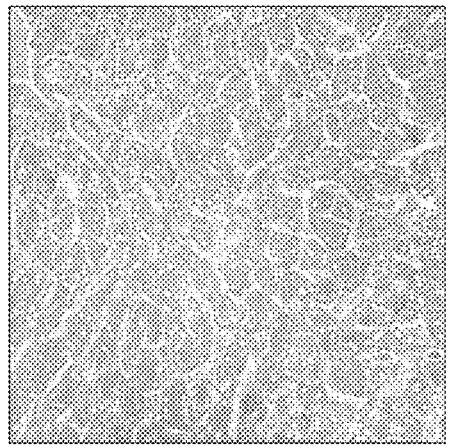
FIG. 3 shows photographs provided instead of drawings and depicting results of microscopic observation of liver tissue sections with Azan staining from mice in a NASH treatment study.
Figure 3:
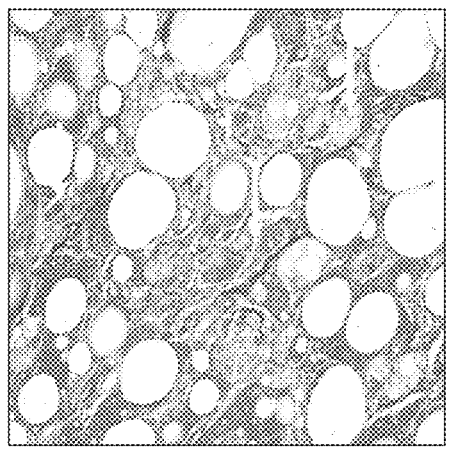
Figure 3:
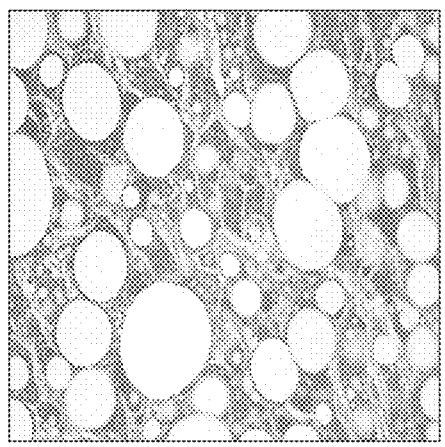

FIG. 3 shows results of microscopic observation of liver tissue sections with Azan staining from those mice.

FIG. 3 (A) is a photograph depicting the result of observation of liver tissue from the control mice, and FIG. 3 (B) is a photograph depicting the result of observation of liver tissue from the NASH mice given a MCDD, and FIG. 3 (C) is a photograph depicting the result of observation of liver tissue from the NASH mice given a MCDD and H-77.

No fat accumulation was observed in the liver tissue from the control mice, as shown in FIG. 3 (A), while an accumulation of fat in the liver tissue was found in the NASH mice given a MCDD, as shown in FIGS. 3 (B) and (C). Moreover, as shown in FIG. 3 (B), fibrosis (the colored area pointed by an arrow) was observed in the liver tissue with Azan staining, in the case where H-77 was not administered. In contrast, as shown in FIG. 3 (C), hepatic fibrosis was significantly inhibited when H-77 was administered.

Example 4

(Cancer Treatment Study)

An animal experiment was performed using mice transplanted with cancer cells to test the therapeutic effects of the compounds according to the present invention on cancer.

A first tumor (DU145 cells) with Matrigel plug was implanted in the middle of the upper back of nude mice (BALB/c-slc-nu/nu mice).

Five weeks after the first implantation, a second tumor (DU145 cells) was implanted in the middle of the left and right sides of the back of the nude mice.

Intraperitoneal administration of a compound according to the present invention, H-77, at a dose of 2.5 mg/kg/day and a frequency of 5 times a week was started 6 weeks after the first implantation, at which the first tumor became measurable (at this timing, the second tumor was so small in size and not measurable), and was continued for 9 weeks. No compound was administered to a group of mice to prepare control mice.

Figure 4:
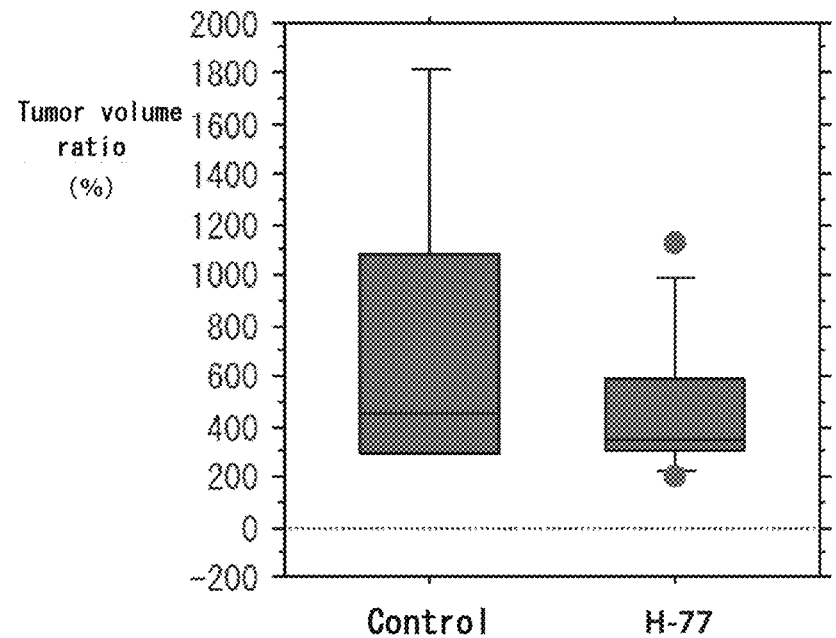
FIG. 4 shows graphs depicting results of measurement of volume change in a first tumor and a second tumor from mice in a cancer treatment study.
Figure 4:
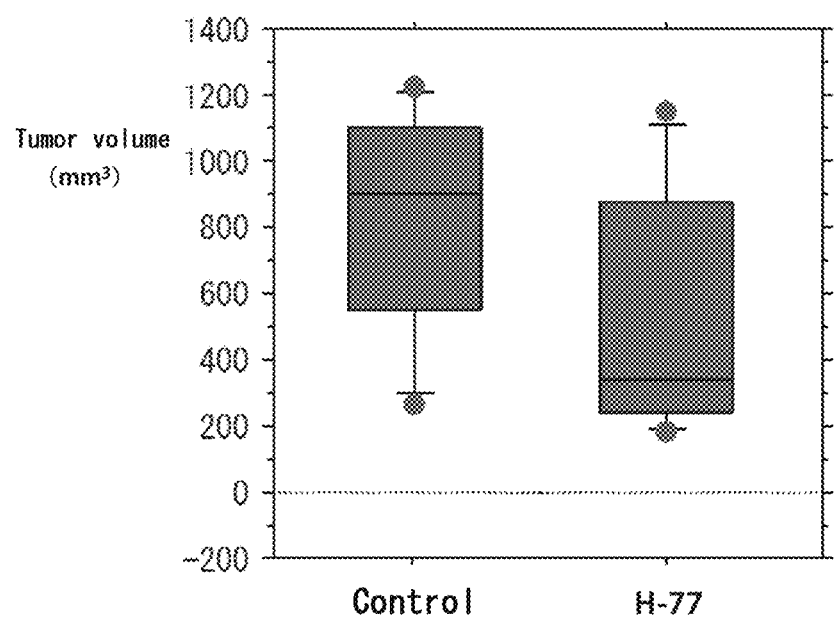

FIG. 4 shows results of measurement of volume change in the first tumor and the second tumor at 9 weeks after the initial administration. FIG. 4 (A) illustrates the distribution of tumor volume ratio (%) in the first tumor at 9 weeks after administration of the compound, where the tumor volume at the beginning of the administration is set as 100, and shows the distribution of size change in the control mice and the mice given H-77, from left to right, expressed in box plot.

As shown in FIG. 4 (A), tumor size growth was suppressed in the mice given H-77 compared to that in the control mice.

FIG. 4 (B) illustrates the distribution of volume of the second tumor and shows the distribution of tumor volume in the control mice and the mice given H-77, from left to right, expressed in box plot. The volume of the second tumor was so small and not measurable at the beginning of administration of the compound. Therefore, the result from the second tumor is expressed in volume (mm$^3$), but not in ratio.

As shown in FIG. 4 (B), tumor size growth was suppressed in the mice given H-77 compared to that in the control mice.

INDUSTRIAL APPLICABILITY

The compounds or salts thereof, Pin1 inhibitors, pharmaceutical compositions, therapeutic or prophylactic agents for inflammatory diseases associated with fibrosis, for cancer, and for obesity according to the present invention are each useful in the pharmaceutical industry.

The invention claimed is:

1. A compound represented by the Formula (I), or a salt thereof:

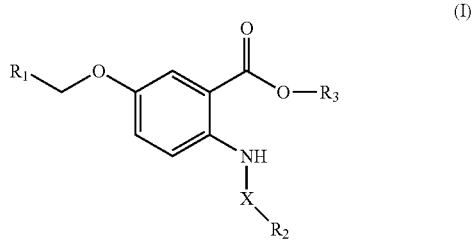

(I)

wherein at least one of the $R_1$ or $R_2$ represents an optionally substituted naphthyl group, an optionally substituted quinolyl group, or an optionally substituted phenoxy phenyl group;

either $R_1$ or $R_2$ represents, if not any of the above-described groups, an optionally substituted aryl group, or an optionally substituted monocyclic heterocyclic group;

$R_3$ represents a hydrogen atom, an optionally substituted hydrocarbon group, or an optionally substituted heterocyclic group; and X represents a single bond, —CO— group, —CO—O—CH$_2$— group, —CO—CH$_2$—O— group, —SO$_2$— group, —CH$_2$—CO—NH— group, —CH$_2$—CO— group, or —CH$_2$— group.

2. The compound or a salt thereof according to claim 1, wherein at least one of $R_1$ or $R_2$ represents an optionally substituted naphthyl group.

3. The compound or a salt thereof according to claim 2, wherein $R_1$ represents an optionally substituted naphthyl group.

4. The compound or a salt thereof according to claim 1, wherein $R_3$ represents a hydrogen atom or a methyl group.

5. A Pin1 inhibitor comprising the compound or a salt thereof according to claim 1.

6. A pharmaceutical composition comprising the compound or a pharmaceutically acceptable salt thereof according to claim 1 and a pharmaceutically acceptable carrier.

7. A therapeutic or prophylactic agent for the treatment or prevention of an inflammatory disease associated with fibrosis, comprising the compound or a pharmaceutically acceptable salt thereof according to claim 1 as an active ingredient.

8. The therapeutic or prophylactic agent according to claim 7, wherein the inflammatory disease associated with fibrosis is non-alcoholic steatohepatitis, inflammatory bowel disease, or pulmonary fibrosis.

9. The therapeutic or prophylactic agent according to claim 7, further comprising an active ingredient of at least one additional drug for the treatment or prevention of the inflammatory disease associated with fibrosis.

10. A method of treating or preventing an inflammatory disease associated with fibrosis, comprising administering the therapeutic or prophylactic agent according to claim 7, in combination with at least one additional drug for the treatment or prevention of the inflammatory disease associated with fibrosis.

11. A therapeutic or prophylactic agent for the treatment or prevention of cancer, comprising the compound or a pharmaceutically acceptable salt thereof according to claim 1 as an active ingredient.

12. The therapeutic or prophylactic agent according to claim 11, wherein the cancer is colon cancer or prostate cancer.

13. The therapeutic or prophylactic agent according to claim 11, further comprising an active ingredient of at least one additional drug for the treatment or prevention of cancer.

14. A method of treating or preventing cancer, comprising administering the therapeutic or prophylactic agent according to claim 11, in combination with at least one additional drug for the treatment or prevention of cancer.

15. A method of preparing a medicament for the treatment or prevention of cancer, comprising combining a pharmaceutically acceptable carrier and a therapeutic or prophylactic amount of the compound or a pharmaceutically acceptable salt thereof according to claim 1.

16. A method of treating or preventing cancer, comprising administering the compound or a pharmaceutically acceptable salt thereof according to claim 1 to a patient in need thereof.

17. A therapeutic or prophylactic agent for the treatment or prevention of obesity, comprising the compound or a pharmaceutically acceptable salt thereof according to claim 1 as an active ingredient.

18. A therapeutic or prophylactic agent according to claim 17, further comprising an active ingredient of at least one additional drug for the treatment or prevention of obesity.

19. A method of treating or preventing obesity, comprising administering the therapeutic or prophylactic agent according to claim 17, in combination with at least one additional drug for the treatment or prevention of obesity.

20. A method of preparing a medicament for the treatment or prevention of obesity, comprising combining a pharmaceutically acceptable carrier and a therapeutic or prophylactic amount of the compound or a pharmaceutically acceptable salt thereof according to claim 1.

21. A method of treating or preventing obesity, comprising administering the compound or a pharmaceutically acceptable salt thereof according claim 1 to a patient in need thereof.

22. A method of preparing a medicament for the treatment or prevention of an inflammatory disease associated with fibrosis, comprising combining a pharmaceutically acceptable carrier and a therapeutic or prophylactic amount of the compound or a pharmaceutically acceptable salt thereof according to claim 1.

23. A method of treating or preventing an inflammatory disease associated with fibrosis, comprising administering the compound or a pharmaceutically acceptable salt thereof according to claim 1 to a patient in need thereof.

24. The compound or a salt thereof according to claim 2, wherein $R_2$ represents an optionally substituted naphthyl group.

* * * * *